United States Patent [19]
Smith, III et al.

[11] Patent Number: 6,034,247
[45] Date of Patent: *Mar. 7, 2000

[54] OXAZOLIDINONES AND METHODS FOR THE SYNTHESIS AND USE OF SAME

[75] Inventors: Amos B. Smith, III, Merion; Ralph F. Hirschmann, Blue Bell; Paul A. Sprengeler, Philadelphia; Andrew B. Benowitz, Willow Grove; David A. Favor, Glenside, all of Pa.

[73] Assignee: The Trustees of the University of Pennsylvania, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/843,031

[22] Filed: Apr. 11, 1997

Related U.S. Application Data

[63] Continuation-in-part of application No. 08/285,027, Aug. 2, 1994, Pat. No. 5,770,732, which is a continuation-in-part of application No. 08/018,696, Feb. 17, 1993, Pat. No. 5,489,692.

[51] Int. Cl.[7] .................................................. C07D 263/04
[52] U.S. Cl. ............................................................ 548/228
[58] Field of Search ............................................ 548/228

[56] References Cited

U.S. PATENT DOCUMENTS

| | | | |
|---|---|---|---|
| 4,264,771 | 4/1981 | Steglich et al. | 548/228 |
| 4,885,292 | 12/1989 | Ryono et al. | 514/424 |
| 5,075,302 | 12/1991 | Neustadt | 514/424 |
| 5,489,692 | 2/1996 | Hirschmann et al. | 548/519 |
| 5,514,814 | 5/1996 | Hirschmann et al. | 548/518 |

OTHER PUBLICATIONS

Seebach et al., "Self–Regeneration of Stereocenters (SRS)—Applications, Limitation, and Abandonment of a Synthetic Principle", Angew. Chem. Int. Ed. Engl., 1996, 35, 2708–2748.

Atherton and Sheppard, "The Fluorenylmethoxycarbonyl Amino Protecting Group", from *The Peptides vol. 9*, Gross and Meienhofer Eds. Academic Press, New York, NY 1–38 (1983).

Corey and Suggs, "Cleavage of Allyloxycarbonyl Protecting Group from Oxygen and Nitrogen Under Mild Conditions by Nickel Carbonyl", *J. Org. Chem.* 38: 3223–3224 (1973).

Iizuka et al., "New Human Renin Inhibitors Containing an Unnatural Amino Acid, Norstatine", *J. Med. Chem.* 31: 701–704 (1988).

Karady et al., "Enantioretentive Alkylation of Acyclic Amino Acids", *Tetrahedron Letters* 25: 4337–4340 (1984).

Kunz et al., "The Allyloxycarbonyl (Aloe) Moiety–Conversionof an Unsuitable into a Valuable Amino Protecting Group for Peptide Synthesis", *Angew. Chem. Int. Ed. Engl.* 23: 436–437 (1984).

Luly et al., "Renin Inhibitors. Dipeptide Analogues of Angiotensinogen Utilizing a Dihydroxyethylene Transition--State Mimic at the Scissile Bond to Impart Greater Inhibitory Potency", *J. Med. Chem.* 31: 2264–2276 (1988).

Magrath and Abeles, "Cysteine Protease Inhibition by Azapeptide Esters", *J. Med. Chem.* 35: 4279–4283 (1992).

Renaud et al., "Mapping of the S' Subsites of Porcine Pancreatic and Human Leucocyte Elastases", *J. Biol. Chem.* 258: 8312–8316 (1983).

Seebach and Fadel, "N, O–Acetals from Pivalaldehyde and Amino Acids for the α–Alkylation with Self Reproduction of the Center of Chirality. Enolates of 3–Benzoyl–2–(tert–butyl)–1, 3–oxazolidin–5–ones", *Helvetica Chimica Acta* 68: 1243–1250 (1985).

Veber et al., "Isonicotinyloxycarbonyl, a Novel Amino Protecting Group for Peptide Synthesis", *J. Org. Chem.* 42: 3286–3288 (1977).

Wlodawer et al., "Conserved Folding in Retroviral Proteases: Crystal Structure of a Synthetic HIV–1 Protease", *Science* 245: 616–621 (1989).

Heimbach, et al., "Affinity Purification of the HIV–1 Protease" *Biochem. Biophys. Res. Commun.* 164: 955–960 (1989).

Thompson, et al., "Synthesis and Antiviral Activity of a Series of HIV–1 Protease Inhibitors with Functionally Tethered to the $P_1$ abd $P_1$ ' Phenyl Substituents: X–ray Crystal Structure Assisted Design" *J. Med. Chem.* 35: 1685–1701 (1992).

Bolis, G. et al., "Renin Inhibitors. Dipeptide analogues of angiotensinogen incorporating transition–state, nonpeptide replacements at the scissile bond" *J. Med. Chem.* 30: 1729–1737 (1987).

Harber, E. et al., "Renin Inhibitors. A Search for Principles of Design" J. of Cardiovascular Pharm. 10: S54–S58 (1987).

*Primary Examiner*—Mukund J. Shah
*Assistant Examiner*—Brenda Coleman
*Attorney, Agent, or Firm*—Woodcock Washburn Kurtz Mackiewicz & Norris LLP

[57] ABSTRACT

Synthetic methods for pyrrolinone-based compounds are provided. Such compounds mimic or inhibit the biological and/or chemical activity of peptides.

5 Claims, 14 Drawing Sheets

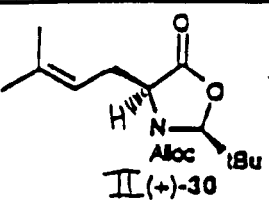

| Amino Acid Analog | E⁺ | Step 2 | R |
|---|---|---|---|
| Alanine | MeI | None | Me |
| Histidine | 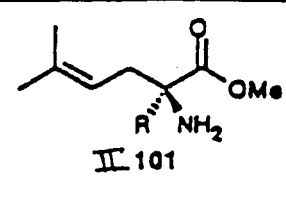 | None |  |
| Serine | BnOCH₂Cl | None | BnOCH₂ |
| Tryptophan |  | None | 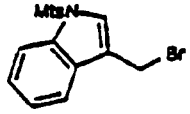 |
| Tyrosine | 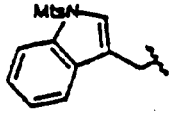 | None | 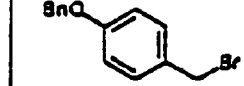 |
| Asparagine | NCCH₂Br | a) Aq H₂SO₄  b) Bn₂NH, DCC | 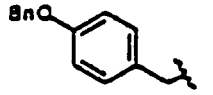 |
| Glutamine | NCCH=CH₂ | a) Aq H₂SO₄  b) Bn₂NH, DCC | 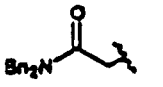 |
| Lysine | I(CH₂)₄I | NaN₃, DMSO | N₃(CH₂)₄ |
| Arginine | 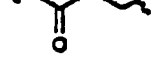 | None | 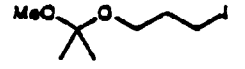 |
| Cysteine | PMBOCH₂Cl | None | PMBOCH₂ |
| Glutamic Acid | SEMO(CH₂)₃I | None | SEMO(CH₂)₃ |
| Aspartic Acid | 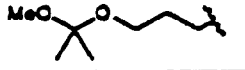, Et₂AlCl | SEMCl, Et₃N | SEMO(CH₂)₂ |
| Methionine | 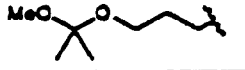, Et₂AlCl | 3,4-DMBCl, NaH | 3,4-DMBO(CH₂)₂ |

Figure 13

| Amino Acid Analog | E⁺ | Step 2 | R |
|---|---|---|---|
| Alkylalanine | R'CH₂I | None | R'CH₂ |
| Cyclohexyl-alanine | [cyclohexyl-CH₂-I] | None | [cyclohexyl-CH₂-] |
| 1- or 2-Naphthyl-alanine | [naphthyl-CH₂-Br] | None | [naphthyl-CH₂-] |
| 9-Anthryl-alanine | [anthryl-CH₂-Br] | None | [anthryl-CH₂-] |
| Fluorophenyl-alanine | [F-C₆H₄-CH₂-Br] | None | [F-C₆H₄-CH₂-] |
| Pyridylalanine | [pyridyl-CH₂-Br] | None | [pyridyl-CH₂-] |
| DOPA | [methylenedioxyphenyl-CH₂-Br] | None | [methylenedioxyphenyl-CH₂-] |
| Nor/Homo-lysine | I(CH₂)ₙI | NaN₃, DMSO | N₃(CH₂)ₙ |
| Homoserine | I(CH₂)ₙI | BnOH, K₂CO₃ | BnO(CH₂)ₙ |

Figure 14

OXAZOLIDINONES AND METHODS FOR THE SYNTHESIS AND USE OF SAME

RELATED APPLICATIONS

This application is a continuation-in-part of application Ser. No. 08/285,027, filed Aug. 2, 1994, now U.S. Pat. No. 5,770,732, which is a continuation-in-part of application Ser. No. 08/018,696, filed Feb. 17, 1993, now U.S. Pat. No. 5,489,692, the disclosures of which are hereby incorporated herein by reference in their entirety.

GOVERNMENT SUPPORT

Certain of the inventors have been supported by National Institutes of Health Grant GM-41821.

FIELD OF THE INVENTION

This invention relates to monomeric and polymeric pyrrolinone-based compounds, to the use of pyrrolinone-based compounds in place of amino acids in naturally-occurring or synthetic peptides, and to methods for preparing such compounds.

BACKGROUND OF THE INVENTION

Peptides are implicated in a wide variety of biochemical processes in humans and other mammals. The design of peptide mimics which are resistant to degradation by proteolytic enzymes has become of increasing interest to peptide chemists. A primary goal has been to reduce the susceptibility of mimics to cleavage and inactivation by peptidases while maintaining certain desired biological, chemical, and/or physical properties of a targeted peptide. As a result, the design and synthesis of non-peptidal peptidomimetics has emerged as an enterprise spanning organic, bioorganic, and medicinal chemistry. Frequently, the design and/or synthetic considerations which attend development of peptide mimics are not easily resolved. For example, there is mounting evidence that hydrogen bonding involving the amide backbones of peptide hormones and their receptors is not required for receptor binding or activation, but that hydrogen bonding involving the amide backbone plays a critical role in the binding of peptidal inhibitors to proteolytic enzymes. Because non-peptidal enzyme inhibitors must mimic both the β-strand conformations and, at least in part, the hydrogen bonding capabilities of their peptide counterparts, the design of such inhibitors is considerably more difficult than the design of non-peptidal hormone-receptor ligands.

There remains a need in the art for metabolically stable chemical compounds which effectively mimic the biological, chemical and/or physical properties of naturally-occurring or synthetic peptides, particularly those having β-Strand conformations, and for more efficient methods of preparing such compounds.

OBJECTS OF THE INVENTION

It is one object of the present invention to provide compounds that mimic or inhibit the biological and/or chemical activity of peptides.

It is another object to provide compounds that are chemically more stable than peptides, particularly under conditions such as found in the human body.

It is yet another object to provide compounds that can assume the conformation of a β-pleated peptide strand.

It is a further object to provide compounds that function as enzyme inhibitors.

It is yet another object to provide simple yet efficient methods for synthesizing such compounds.

SUMMARY OF THE INVENTION

These and other objects are accomplished by the present invention, which provides pyrrolinone-based compounds that mimic or inhibit the biological and/or chemical activity of a target peptide. In a general sense, the compounds of the invention differ from the target peptide in that they contain functionalized pyrrolinone units in place of one or more peptide amino acids. The compounds can be used to modulate the chemical and/or biological activity of enzymes or other peptides. Indeed, compounds containing covalently bound sequences of pyrrolinone units have been found to mimic the β-strand conformation of a number of naturally occurring peptidal inhibitors of proteolytic enzymes.

In certain embodiments, the pyrrolinone-based compounds of the invention include one or more pyrrolinone units having structures (1) and/or (2):

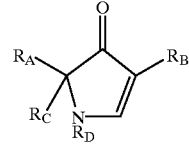

(1)

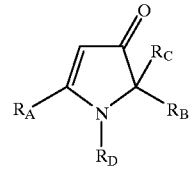

(2)

where:

$R_A$ is a C-terminal amino acid, a C-terminal peptide, or a further pyrrolinone unit;

$R_B$ is a N-terminal amino acid, a N-terminal peptide, or a further pyrrolinone unit;

$R_C$ is a natural or unnatural amino acid side chain; and $R_D$ is H, an amine protecting group, or alkyl having 1 to about 7 carbon atoms.

Certain compounds of the invention have structure (3):

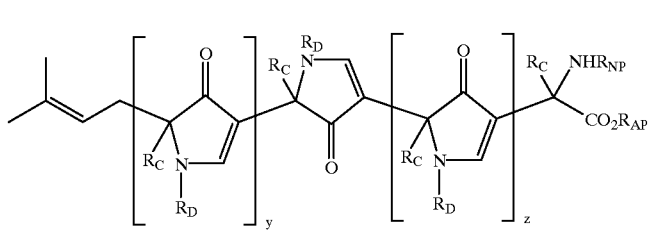

(3)

wherein:
each $R_C$ is, independently, a natural or unnatural amino acid side chain;
each $R_D$ is, independently, H, an amine protecting group, or alkyl having 1 to about 7 carbon atoms;
$R_{NP}$ is H or an amine protecting group;
$R_{AP}$ is H or a carboxyl protecting group; and
y and z are, independently, 0–200.

The compounds of the invention preferably are prepared by a two-step synthesis of 3,5,5-trisubstituted pyrrolin-4-ones that involves intramolecular cyclization of metalated imino esters. The imino esters derive from α,α-disubstiututed amino esters, which preferably are produced by enantioretentive alkylation of oxazolidinones. In certain embodiments, pyrrolin-4-ones having structure (3) are prepared by cyclizing a first synthon having structure (4) and a second synthon having structure (5).

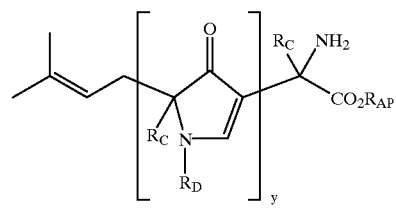

(4)

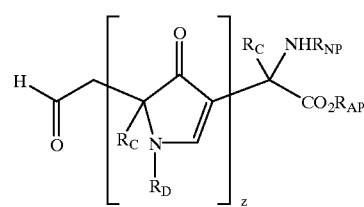

(5)

In one aspect, the present invention provides improved methods for preparing pyrrolinone-based compounds, as well as the synthetic intermediates employed in such methods. Certain methods according to the invention involve reacting compounds of formula (I):

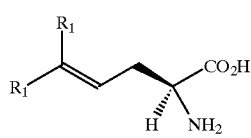

(I)

wherein each $R_1$ is, independently, an alkyl group having from 1 to about 10 carbon atoms; with base, a compound of the formula $R_2$—C(=O)H wherein $R_2$ is an alkyl group having from 1 to about 10 carbon atoms or an aryl group having from about 3 to about 10 carbon atoms, and a compound of the formula $R_3$—X, wherein $R_3$ is an amine protecting group and X is a halogen atom or a suitable leaving group, to produce novel oxazolidinone compounds of formula (II):

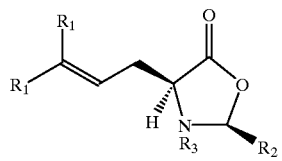

(II)

wherein $R_1$, $R_2$ and $R_3$ are as defined above.

Such oxazolidinone compounds may be alkylated with an electrophile corresponding to a natural or unnatural amino acid side chain to produce a compound of formula (V):

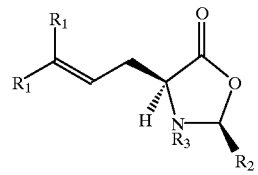

(V)

wherein:
each $R_1$ is, independently, an alkyl group having from to about 10 carbon atoms;
$R_2$ is an alkyl group having from 1 to about 10 carbon atoms or an aryl group having from about 3 to about 10 carbon atoms;
$R_3$ is an amine protecting group; and
$R_5$ is a side chain of a natural or unnatural amino acid.

Thereafter, compounds of formula (V) are reacted in the presence of base to produce compounds of formula (VI):

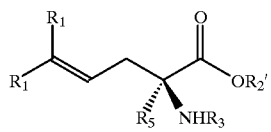

(VI)

wherein $R_1$, $R_3$ and $R_5$ are as defined above, and $R_2$ is an alkyl group having from 1 to about 10 carbon atoms or an aryl group having from about 3 to about 10 carbon atoms.

Compounds of formula (VI) are then reacted in the presence of catalyst to produce compounds of formula (VII):

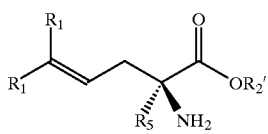

(VII)

wherein $R_1$, $R_2$ and $R_5$ are as defined above.

The pyrrolinone-based compounds of the invention are believed to possess beneficial properties such as increased half-life, lack of immunogenicity, and the ability to cross the blood-brain barrier. They are believed to be useful for the development of pharmaceutical, therapeutic, and diagnostic techniques. Accordingly, the invention provides methods for producing a prophylactic or therapeutic response in a mammal by administering to the mammal a pharmaceutically effective amount of one or more compounds of the invention. In accordance with preferred embodiments, the present invention provides methods for producing such responses by administering an effective amount of a compound of the invention, thereby modulating the activity of a mammalian enzyme.

These and other objects of the present invention are described in further detail below.

BRIEF DESCRIPTION OF THE FIGURES

The numerous objects and advantages of the present invention can be better understood by those skilled in the art by reference to the accompanying figures, in which:

FIG. 13 shows representative syntheses using oxazolidinone compounds to produce imino esters functionalized with various natural or unnatural amino acid side chains.

FIG. 14 shows representative syntheses using novel oxazolidinone compounds to produce imino esters functionalized with various natural or unnatural amino acid side chains.

DETAILED DESCRIPTION OF THE INVENTION

Figure 1:
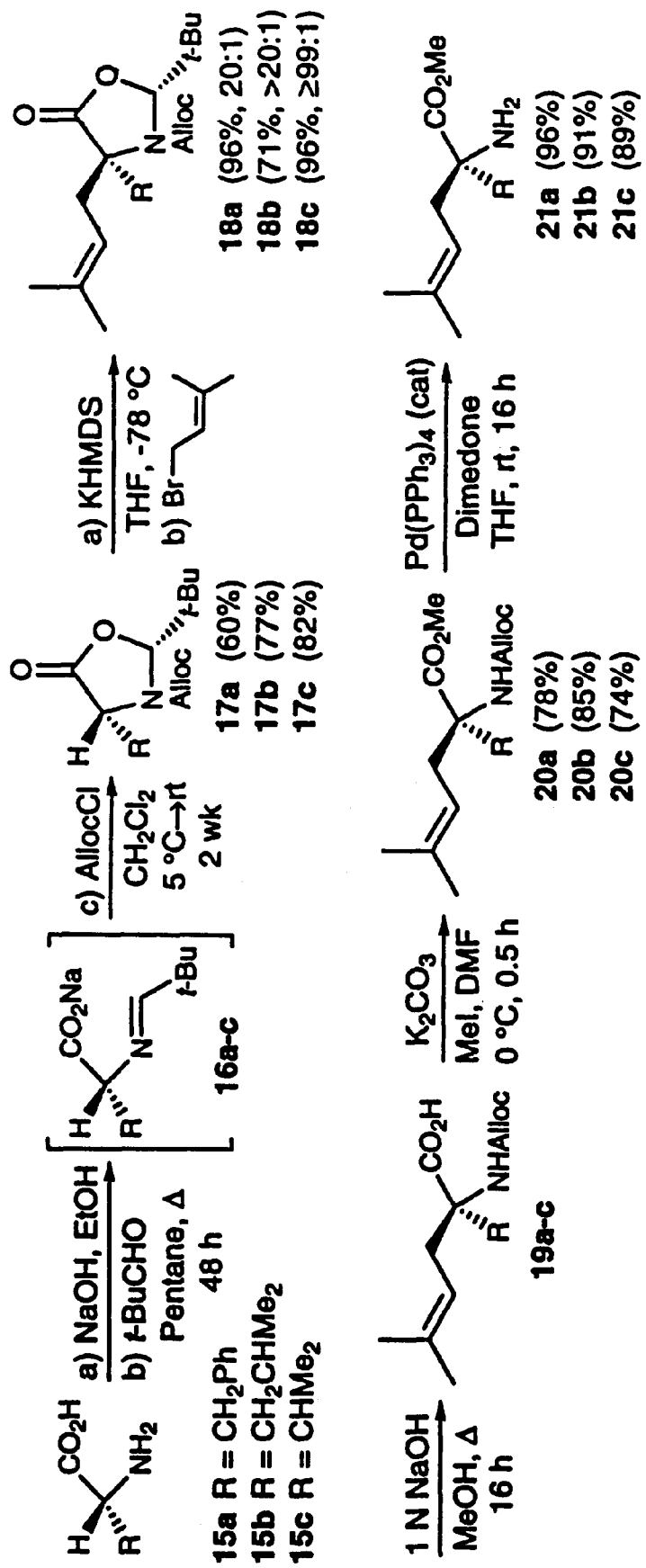
FIG. 1 shows a representative synthesis of acyclic olefinic synthons according to the invention.

It has been found in accordance with the present invention that a new class of compounds containing linked sequences of pyrrolinone units (e.g., structure 6) can adopt backbone conformations that mimic a peptide β-strand, and that peptidal side chains appended to the 5-positions of such units assume desired perpendicular orientations.

By way of example, it is known that structure (7), the crystalline methyl ester of an equine angiotensin fragment, exists as a parallel β-pleated sheet. Comparison of structures (6) and (7) reveals that the disposition of vinylogous amide carbonyls in structure (6) closely correspond with the orientation of the peptide carbonyls in structure (7), maintaining the hydrogen-bond-acceptor capabilities of the native β-strand. The pyrrolinone N—H groups, though vinylogously displaced from the backbone, are comparable to amide nitrogens in basicity and are believed to stabilize the requisite β-strand and β-pleated-sheet conformations through intramolecular and intermolecular hydrogen bonding.

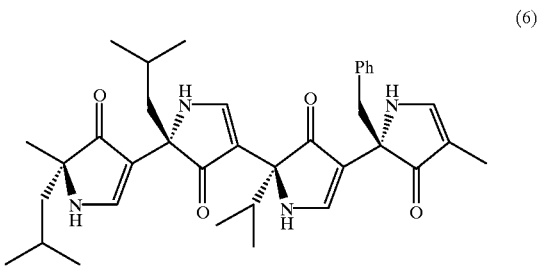

(6)

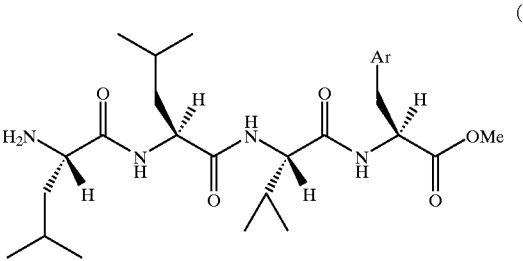

(7)

Certain pyrrolinone-based compounds of the invention include one or more pyrrolinone units having structure (1) and/or (2):

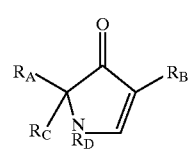

(1)

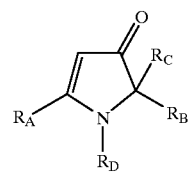

(2)

where:
$R_A$ is a C-terminal amino acid, a C-terminal peptide, or a further pyrrolinone unit;
$R_B$ is a N-terminal amino acid, a N-terminal peptide, or a further pyrrolinone unit;
$R_C$ is a natural or unnatural amino acid side chain; and
$R_D$ is H, an amine protecting group, or alkyl having 1 to about 7 carbon atoms.

In preferred embodiments, compounds of the invention include pyrrolinone-based structures (8a) and (8b):

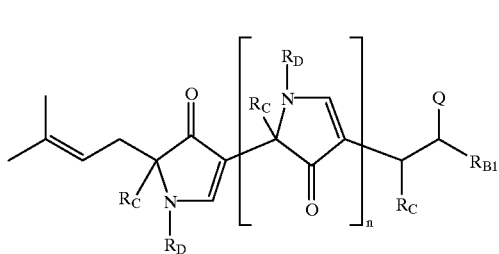
(8a)

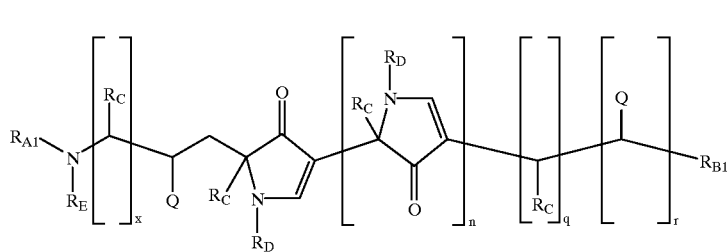
(8b)

where:

- $R_{A1}$ is H, a C-terminal amino acid, a C-terminal peptide, an amine protecting group, an amide protecting group, a group that improves the pharmacokinetic properties of the compound, or a group that improves the pharmacodynamic properties of the compound;
- $R_{B1}$ is $OR_D$, $NR_DR_D$, a N-terminal amino acid, a N-terminal peptide, a carboxyl protecting group, a group that improves the pharmacokinetic properties of the compound, or a group that improves the pharmacodynamic properties of the compound;
- each $R_C$ is, independently, a natural or unnatural amino acid side chain;
- $R_D$ is H, an amine protecting group, or alkyl having 1 to about 7 carbon atoms;
- $R_E$ is H or an amine protecting group, or $R_{A1}$ and $R_E$, together are a group that improves the pharmacokinetic properties of the compound or a group that improves the pharmacodynamic properties of the compound;
- each Q is, independently, OH or $=O$;
- n is 0–200;
- q is 0 or 1;
- r is 0 or 1; and
- x is 0 or 1.

In preferred embodiments, $R_{A1}$ has structure —C(X)— X—$R_F$ wherein each X is, independently, O or S, $R_F$ is alkyl having 1 to about 12 carbon atoms or heterocycloalkyl having 3 to about 6 carbon atoms, and said heteroatomic moiety is selected from O, NH, S, $SO_2$. Particularly preferred $R_F$ include —$C(CH_3)_3$ and the following structures:

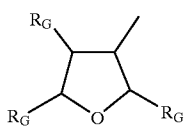 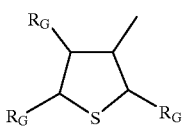

-continued

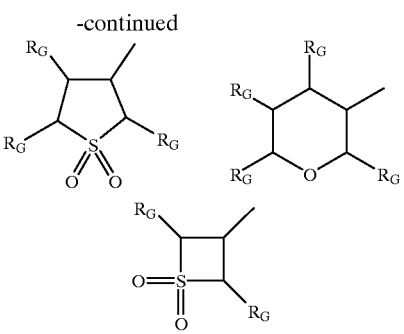

wherein each $R_G$ is, independently, H or alkyl having 1 to about 12 carbon atoms. In certain embodiments, $R_{A1}$—N—$R_E$, together, have structure:

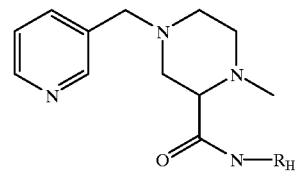

wherein $R_H$ is H or alkyl having 1 to about 12 carbon atoms.

$R_{B1}$ preferably is an amine group, $NHR_I$, where $R_I$ is H or alkyl having 1 to about 12 carbon atoms, or alkoxy having 1 to about 12 carbon atoms. In certain embodiments, $R_{B1}$ is a cyclic or polycyclic, aromatic or non-aromatic functionalized hydrocarbon, such as, for example:

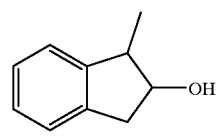

In embodiments in which only a single pyrrolinone group is present (i.e., n=1), q and r preferably are each 0.

Representative compounds of the invention have structures (9)–(12), (49), (53), (54), (58), (59), (67), or (68). Structure (9a) at 3.5 μM and structure (11) at 10 nM have been found to act as effective HIV1 inhibitors. (see, e.g., Wlodawer, et al., *Science* 1989, 245, 616.). Structure (10a) at 700 nM has been found to act as an effective renin inhibitor. Structure (12) is believed to be an effective serine protease inhibitor (see, e.g., Renaud, et al., *J. Biol. Chem.* 1983, 258, 8312.).

(9a)
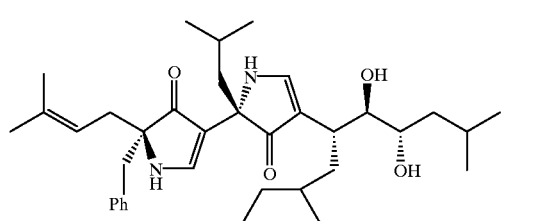

(9b)
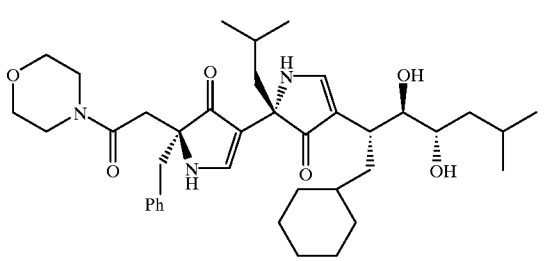

(10a)
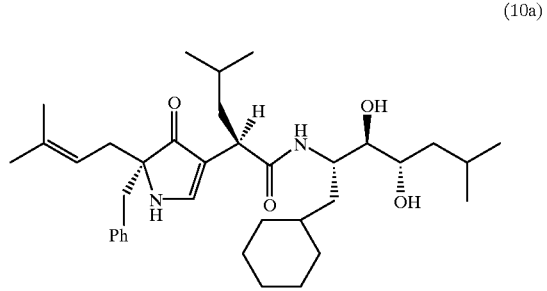

(10b)
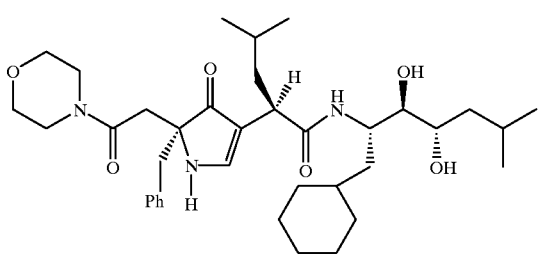

(11)
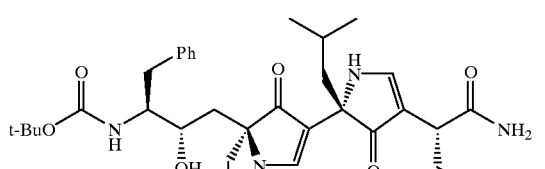

(12)
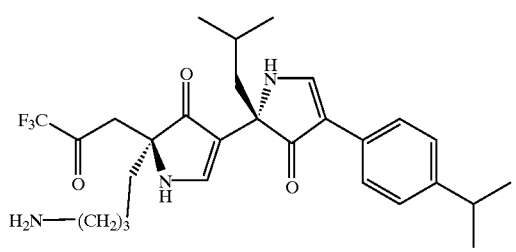

The term amino acid as used herein is intended to include all naturally-occurring and synthetic (unnatural) amino acids known in the art. As will be recognized, amino acids have both C-terminal and N-terminal ends, either of which can be covalently bound to the compounds of the invention. In general, amino acids have structure $H_2N—CH(R_C)—C(O)OH$ where $R_C$ is the amino acid side chain. Representative, naturally-occurring side chains are shown in Table 1.

TABLE 1

$CH_3—$
$HO—CH_2—$
$C_6H_5—CH_2—$
$HO—C_6H_5—CH_2—$

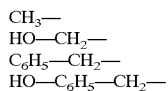

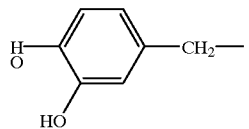

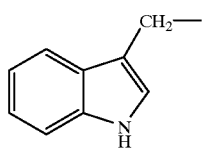

$HS—CH_2—$
$HO_2C—CH(NH_2)—CH_2—S—S—CH_2—$
$CH_3—CH_2—$
$CH_3—S—CH_2—CH_2—$
$CH_3—CH_2—S—CH_2—CH_2—$
$HO—CH_2—CH_2—$
$CH_3—CH_2(OH)—$
$HO_2C—CH_2—NH_2C(O)—CH_2—$

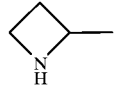

TABLE 1-continued

HCO$_2$—CH$_2$—CH$_2$—
NH$_2$C(O)—CH$_2$—CH$_2$—
(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—
H$_2$N—C(NH)—NH—CH$_2$—CH$_2$—CH$_2$—
H$_2$N—C(O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

Preferred side chains include (CH$_3$)$_2$—CH—, (CH$_3$)$_2$—CH—, (CH$_3$)$_2$—CH—CH$_2$—, C$_6$H$_5$—CH$_2$—, and R$_f$C(O)C(O)—(CH$_2$)$_z$—O—C$_6$H$_5$—CH$_2$— where z is 1 to about 10 (preferably 1–6) and R$_f$ is H or alkyl having 1 to about 12 carbon atoms. Peptides according to the invention are linear, branched, or cyclic chemical structures containing at least 2 covalently bound amino acids. Like individual amino acids, peptides can be incorporated into the compounds of the invention through C-terminal or N-terminal positions.

Alkyl groups according to the invention include but are not limited to straight chain, branched chain, and cyclic hydrocarbons such as methyl, ethyl, propyl, pentyl, isopropyl, 2-butyl, isobutyl, 2-methylbutyl, and isopentyl moieties having 1 to about 12 carbon atoms, preferably 1 to about 7 carbon atoms.

Protecting groups are known per se as chemical functional groups that can be selectively appended to and removed from functionality, such as amine groups, present in a chemical compound to render such functionality inert to chemical reaction conditions to which the compound is exposed. See, e.g., Greene and Wuts, Protective Groups in Organic Synthesis, 2d edition, John Wiley & Sons, New York, 1991. Numerous amine protecting groups are known in the art, including the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38). For example, it is known that the Boc group can protect an amine group from base and from reducing conditions but that it can be removed with acid. Carboxyl protecting groups also are known, including lower (i.e., C$_1$–C$_7$) alkyl esters and benzyl esters. Preferred carboxyl protecting groups are stable to acid but can be removed with base.

Groups that improve pharmacokinetic properties are chemical functional groups that improve uptake, enhance resistance to degradation, and/or strengthen enzyme or receptor binding. Groups that enhance pharmacokinetic properties are chemical functional groups that improve uptake, distribution, metabolism or excretion. Indeed, many groups for improving pharmacokinetic and/or pharmacodynamic properties of peptides are known to those skilled in the art. For example, the terminal morpholino and NH—CH (CH$_2$-C$_6$H$_{11}$)—CH(OH)—CH(OH)—CH$_2$—CH(CH$_3$)$_2$ groups of structure (10b) have been shown by Iizuka, et al. *J. Med. Chem.* 1988, 31, 701, and Luly, et al., *J. Med. Chem* 1988, 31, 2264, respectively, to improve the binding affinity of renininhibiting peptides. Also, Magrath and Abeles, *J. Med. Chem.* 1992, 35, 4279, disclose use of trifluoromethyl and diazomethyl groups at the C-terminal (R$_{B1}$) position to enhance selectivity for serine and cysteine proteases, respectively.

It will be recognized that the number and structural arrangement of pyrrolinone units in the compounds of the invention can be highly variable. For example, useful mimics for a naturally-occurring tetrapeptide (7) are believed to include poly-pyrrolinone (6) as well as mono-pyrrolinone (13).

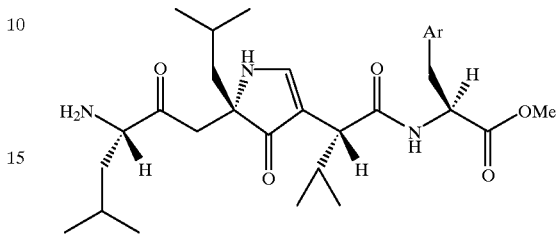

(13)

It is believed that compounds containing a series of at least about 3 covalently bound pyrrolinone units (e.g., n=3) best mimic the β-conformation of a peptide strand, although 2 units are sufficient. However, structure generally is dictated by functional concerns or, more frequently, a balancing of competing functional concerns. Thus, in a hypothetical system in which structures (6) and (13) exhibit comparable binding affinity for a given enzyme but structure (6) exhibits markedly greater stability, structure (6) typically will be preferred. In addition, it will be recognized that 3,5,5-trisubstituted pyrrolin-4-one units (e.g., structure (1)) and 2,5,5-trisubstituted pyrrolin-4-one units (e.g., structure (2)) can be used interchangeably.

In certain embodiments, the compounds of the invention are prepared by a two-step synthesis of scalemic 3,5,5-trisubstituted pyrrolin-4-ones that employs intramolecular cyclization of metalated imino esters. The imino esters, in turn, derive from α,α-disubstituted amino esters, the latter being readily available via enantioretentive alkylation of oxazolidinones. As shown in FIG. 1, construction of the α-alkylated amino esters begins with formation of the pivaldehyde imines of D-phenylalanine (15a), D-leucine (15b), and D-valine (15c) via the Seebach protocol (see, e.g., Seebach, et al., *Helv. Chim. Acta* 1985, 68, 1243). Treatment of the imines (16c) with allyl chloroformate generally in accordance with Corey, et al., *J. Org. Chem.* 1973, 38, 3223, induced cyclization to furnish cisoxazolidinones (17a–c). Interestingly, exposure to Boc anhydride did not produce the corresponding oxazolidinone. Enantioretentive alkylation as described by Seebach (i.e., KHMDS, prenyl bromide, THF, –78° C.) afforded oxazolidinones (18a–c) with greater than 95% diastereoselectivity. Hydrolysis to Alloc-protected amino acids (19a–c) then was achieved generally according to Karady, et al., *Tetrahedron Lett.* 1984, 25, 4337 (1 N NaOH, MeOH, reflux, 16 h), and the resultant acids were immediately methylated [K$_2$CO$_3$ (2.5 equiv), MeI (2 equiv), DMF, 0.5 h] to furnish esters (20a–c). The Alloc protecting groups could be removed in the presence of the prenyl group with catalytic Pd(PPh$_3$)$_4$ and dimedone (5 equiv; see, e.g., Kunz, et al., *Angew. Chem. Int. Ed. Engl.* 1984, 23, 436), providing the desired α-alkyl amino esters (21a–c) after Kugelrohr distillation. This sequence is both efficient (42–52% yields for the 6-step sequence) and amenable to large-scale production (ca. 100 g).

Figure 2:
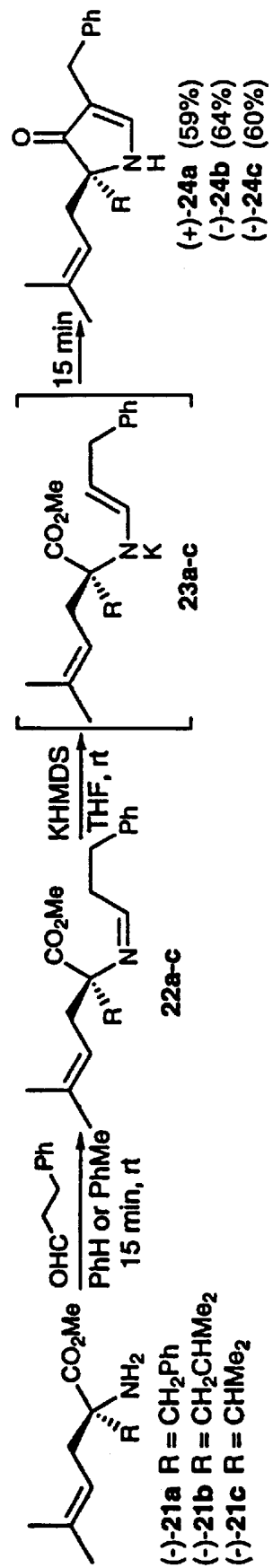
FIG. 2 shows a cyclization procedure according to the invention.

As shown in FIG. 2, amino ester (21a) was condensed with hydrocinnamaldehyde (1.1 equiv) by in vacuo concentration of a benzene or toluene solution of the compounds at ambient temperature; $^1$H NMR analysis verified the formation of imine (22a). Metalation with KHMDS (THF, room temperature) then furnished metallo imine (23a). Upon stirring at room temperature for 15 min, TLC analysis (20% EtOAc/hexanes) revealed the formation of the desired pyrrolinone (24a), isolable in 59% yield overall from (21a). Similar treatment of the imines derived from amines (21b) and (21c) led to heterocycles (24b) and (24c). The use of lithium diisopropylamide (LDA) for metalation afforded lower yields of the pyrrolinones.

Figure 3:
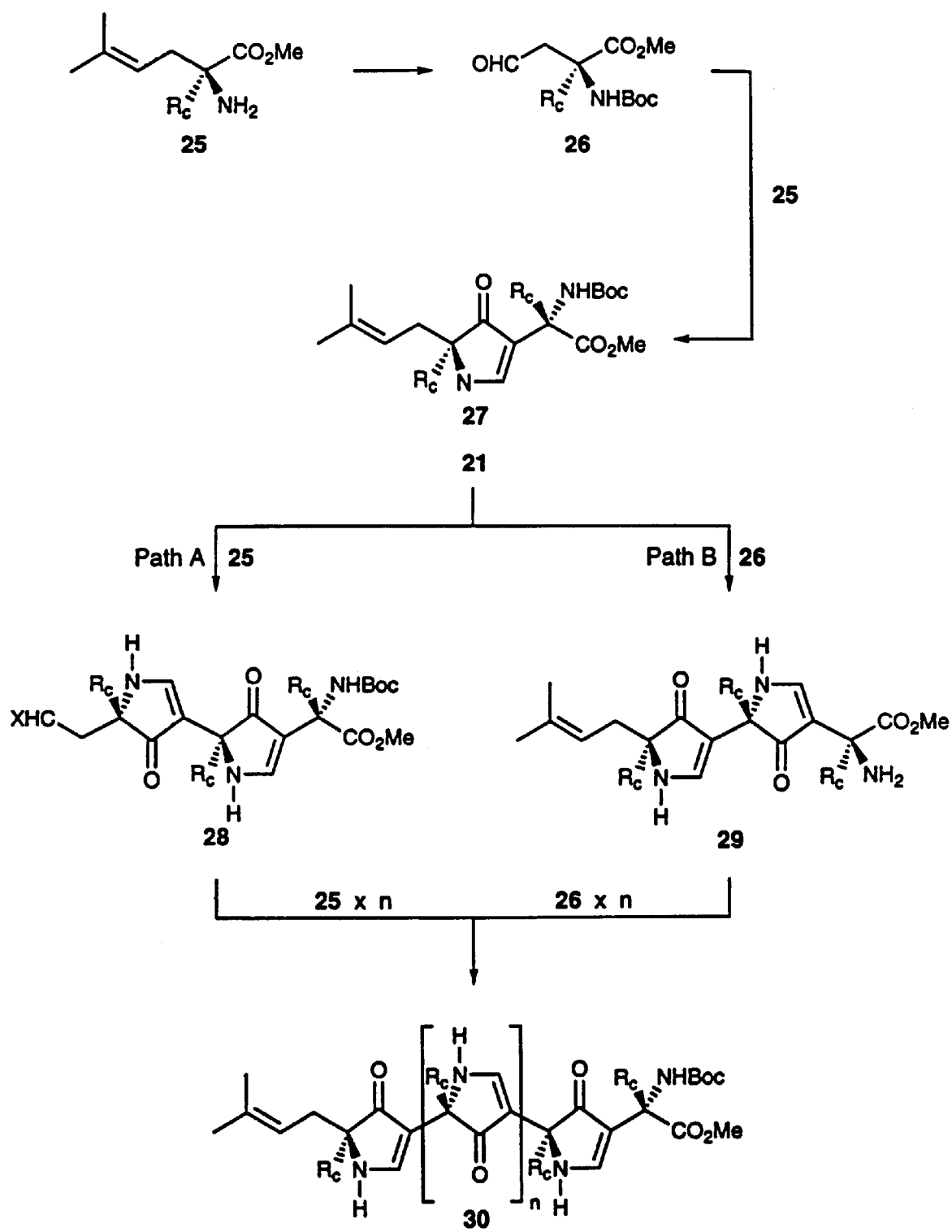
FIG. 3 shows representative syntheses of compounds of the invention via N-terminal and C-terminal cyclizations.

Extension of this procedure to the iterative formation of linked pyrrolinones, as in FIG. 3, can furnish, for example, structure (30) by either "N-terminal" or "C-terminal" elaboration. As will be recognized, N-terminal elaboration is exemplified by Path A, wherein X=$O_2$Me (28a) or X=O (28b), and C-terminal elaboration is exemplified by Path B.

Figure 4:
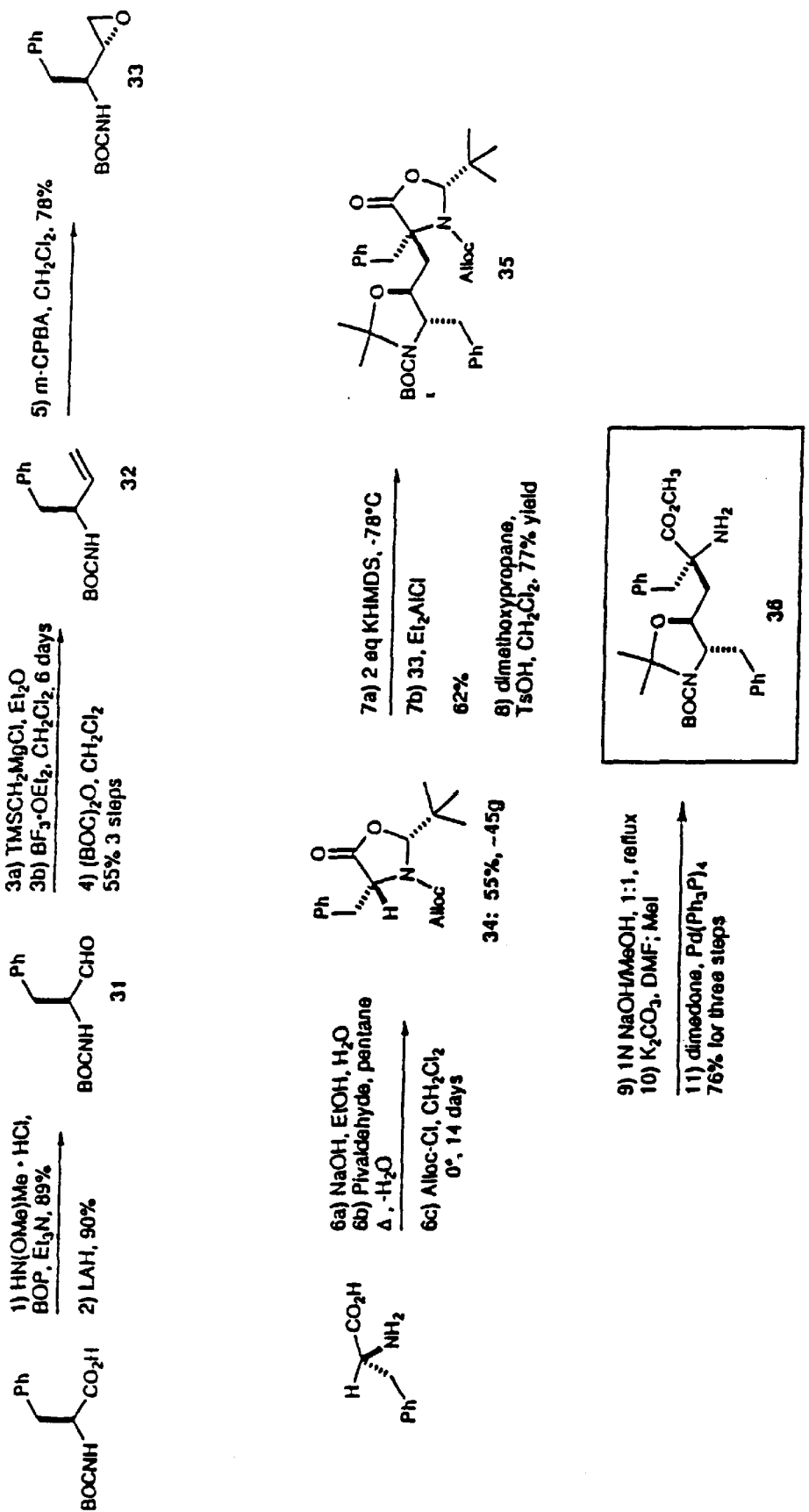
FIG. 4 shows a representative synthesis of chemical intermediate (36).

The synthesis of building block (36) (shown in FIG. 4) began with t-butyl carbamate protected L-phenylalanine. Conversion to the corresponding Weinreb amide (N-methyl-O-methyl hydroxylamine,benzotriazol-1-yloxytris-(dimethylamino)-phosphonium hexafluorophosphate (BOP) and triethylamine, 89%) followed by lithium aluminum hydride (LAH) reduction (90%) afforded aldehyde (31). Peterson Olefination (trimethylsilylmethyl Grignard reagent; $BF_3 \cdot OEt_2$) led to the corresponding terminal alkene. The BOC protecting group, which was removed under the reaction conditions, was then replaced using BOC-anhydride, resulting in compound (32) (55% for the three steps). Terminal alkene (32) was subsequently treated with m-chloroperoxybenzoic acid (mCPBA) in methylene chloride to give epoxide (33) (78%). The oxazolidinone (34) (obtained from D-phenylalanine by condensation with pivaldehyde and Alloc-Cl induced cyclization, 55%), was metallated with KHMDS to generate its corresponding enolate, which was alkylated with epoxide (33) in the presence of diethyl aluminum chloride (62%). The hydroxyl and carbamate NH group of the coupled product were simultaneously protected (dimethoxypropane, catalytic tosyl alcohol (TsOH), acetone, 77%) resulting in acetonide (35). Hydrolysis of the oxazolidinone ring (1 N NaOH/methanol, 1:1, reflux 72 h) was followed by methyl ester formation (MeI, $K_2CO_3$, dimethylformamide (DMF)) and deprotection of the amine (cat. Pd(PPh$_3$)4, dimedone, THF, 76% for three steps) afforded aminoester building block (36).

Figure 5:
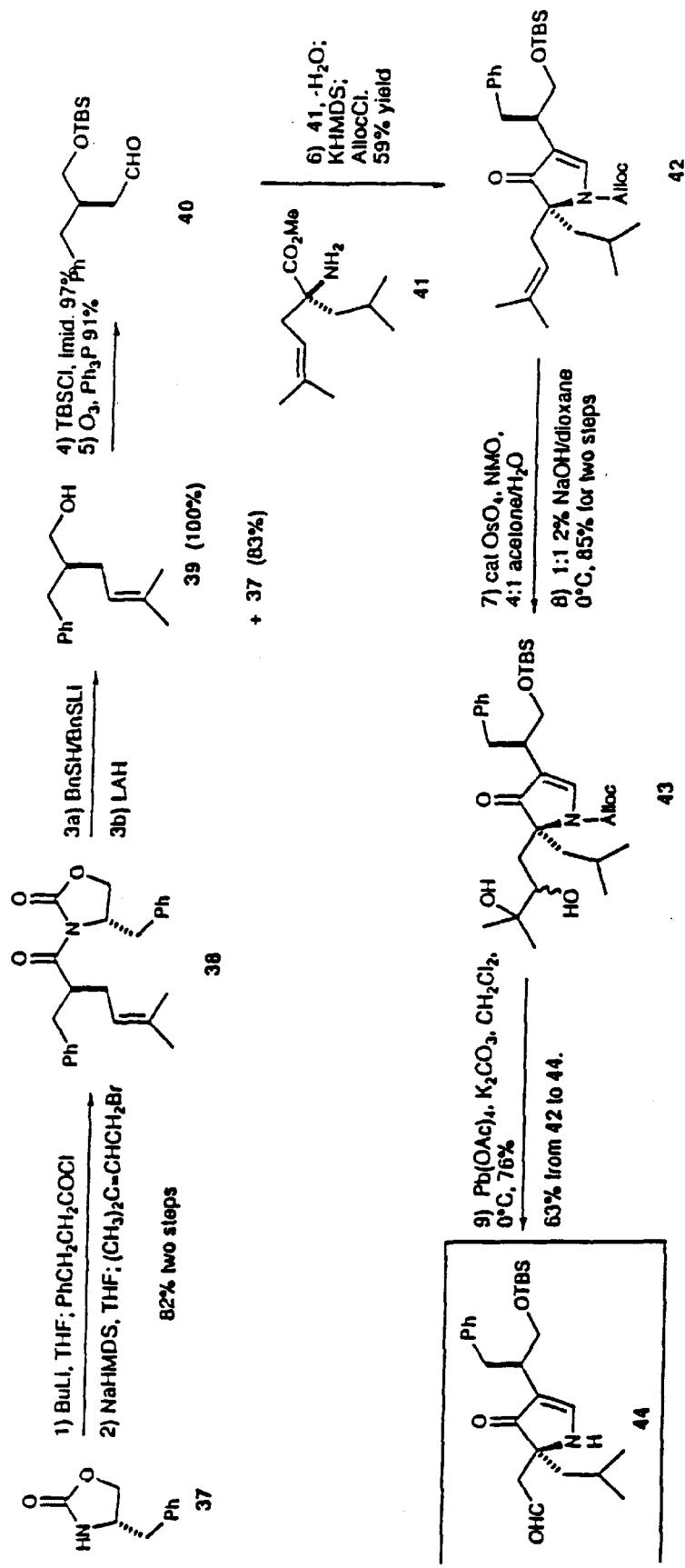
FIG. 5 shows a representative synthesis of chemical intermediate (44).

As shown in FIG. 5, fragment (44) was prepared starting from the Evans-type oxazolidinone (37). Acylation of (37) with hydrocinamoyl chloride, followed by treatment with sodium 1,1,1,3,3,3-hexamethyldisilazide (NaHMDS) to generate the corresponding enolate and subsequent alkylation with prenyl bromide provided compound (38) (82%). Removal of the chiral auxiliary was accomplished by treatment with benzyl thiolate followed by LAH reduction of the resulting thioester (100%). The primary hydroxyl group of (39) was then protected as its t-butyldimethylsilyl (TBS) ether (TBSCl, imidazole, 97%). Ozonolysis ($O_3$, $CH_2Cl_2$, —78° C.) then provided aldehyde (40) (91%). Condensation of aldehyde (40) with aminoester (41), followed by treatment with KHMDS and quenching with Alloc-Cl gave the N-protected pyrrolinone (42) (59%). The prenyl side chain of (42) was hydroxylated with $OsO_4$ and N-methylmorpholine N-oxide monohydrate (NMO). The Alloc protecting group, which was also oxidized under these conditions, was removed with 2% NaOH in dioxane (85% for two steps). The resulting diol (43) was further oxidized to aldehyde (44) by treatment with Pb(OAc)$_4$ (76%).

Figure 6:
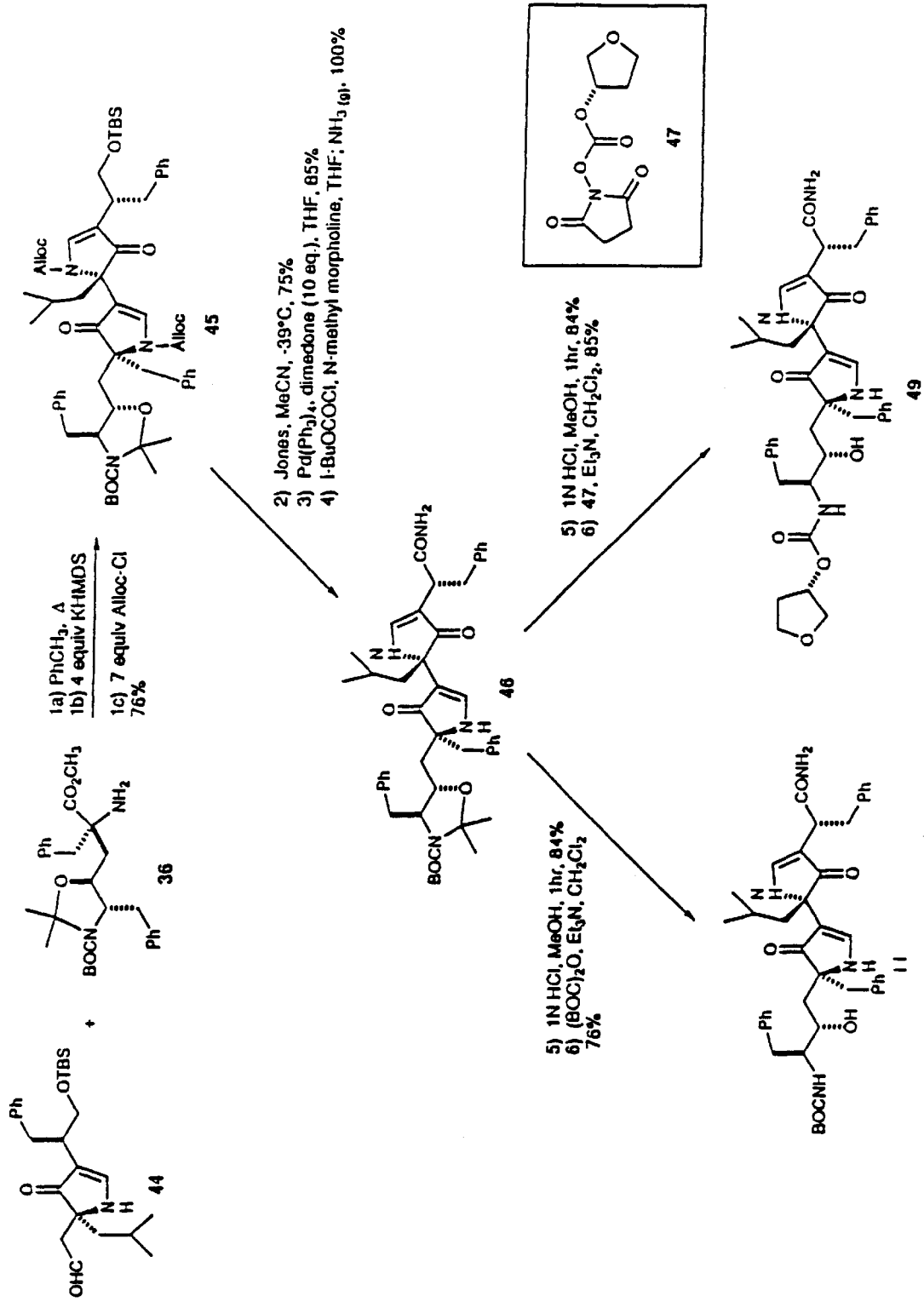
FIG. 6 shows a representative synthesis of compounds (11) and (49).

Fragments (44) and (36) were coupled together (FIG. 6) by condensation, treatment with KHMDS and quenching with Alloc-Cl (76%). The resulting Alloc protected bispyrrolinone (45) was oxidized with Jones reagent (75%), deprotected (Pd(PPh$_{3)4}$, dimedone, THF, 85%) and finally transformed to the corresponding primary amide by aminolysis of the mixed anhydride generated with $_4$isobutylchloroformate to give amide (46) (100%). Intermediate (46) could be converted to the target HIV-1 inhibitor (11) by deprotection of the BOC and acetonide groups (1 N HCl in methanol, 84%), followed by incorporation of the t-butyl carbamate functionality (BOC anhydride, Et$_3$N, $CH_2Cl_2$, 76%). Target inhibitor (49) could be prepared in a similar fashion by deprotection (1N HCl in methanol, 84%), followed by treatment of the corresponding N-terminal amino group with reagent (47) (85%).

Figure 7:
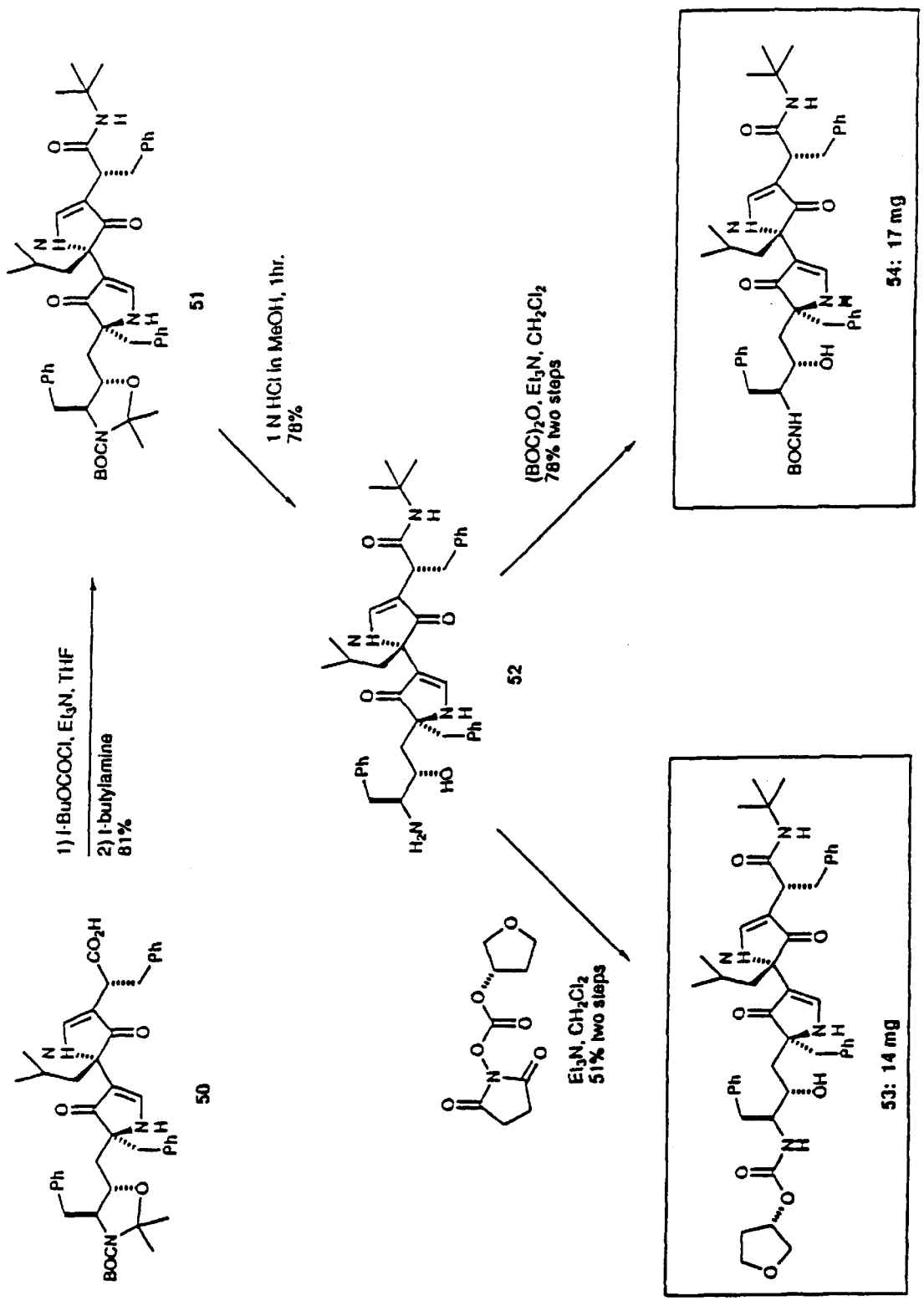
FIG. 7 shows a representative synthesis of compound (53) and (54).

Compound (40), which was obtained during the synthesis of inhibitors (11) and (49) (see FIG. 6) was converted to its corresponding t-butyl amide (51), as shown in FIG. 7, by reaction of an intermediate mixed anhydride (generated with isobutylchloroformate) with t-butyl amine (81%). Removal of the acetonide and BOC protecting groups (iN HCl in methanol, 78%) resulted in amine (52). Amine (52) was then converted to target inhibitor (53) by treatment with carbonate reagent (47) (51% for the two step sequence). Inhibitor (54), in turn, could be prepared by reaction of amine (52) with BOC anhydride (78% for the two step sequence).

Figure 8:
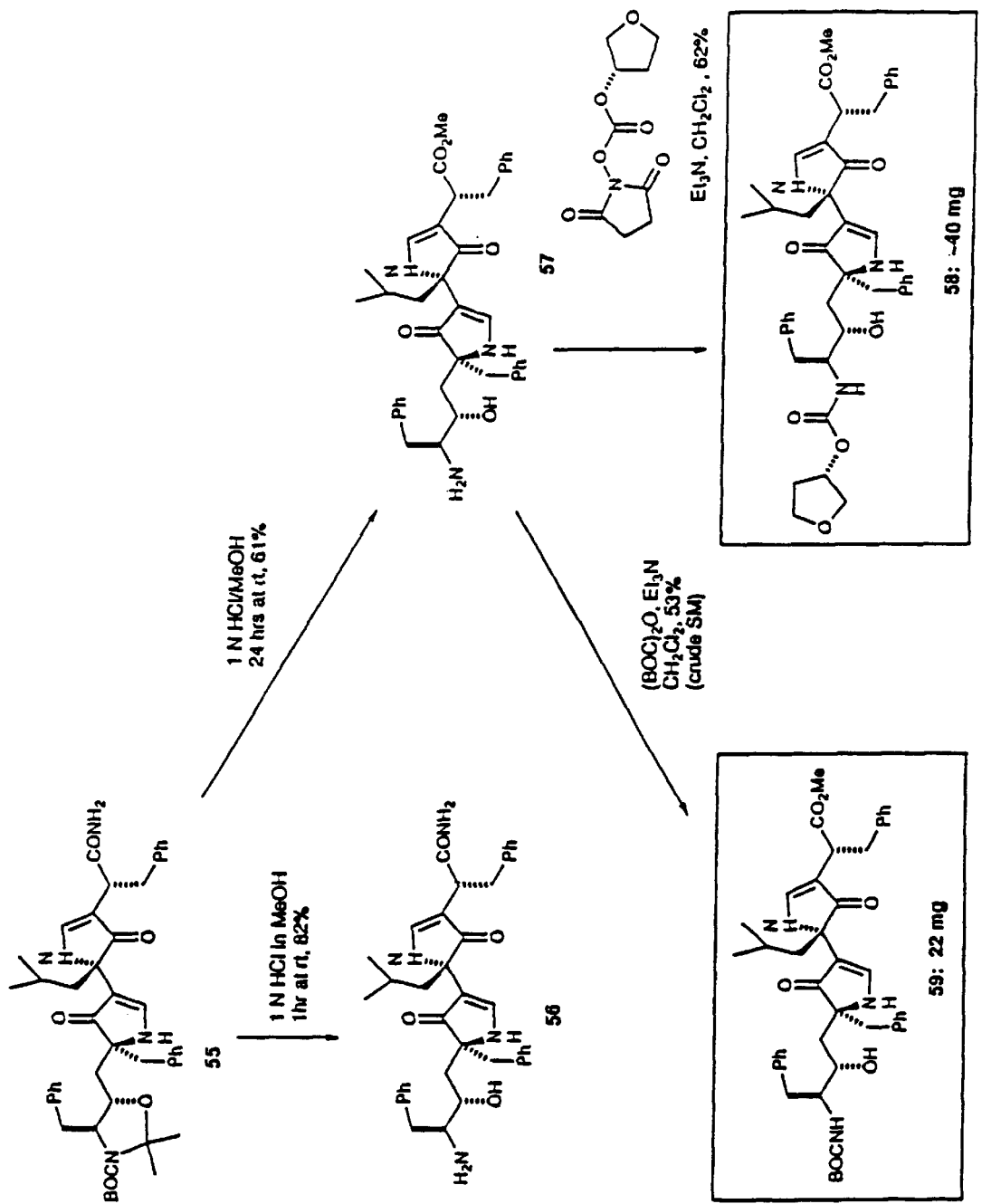
FIG. 8 shows a representative synthesis of compounds (58) and (59).

Treatment of compound (55) (obtained during the synthesis of (11) and (49)) with 1 N HCl in methanol for 24 hours (FIG. 8) to give ester (57) (61%). The same reaction carried out for only one hour results in primary amide (56). Ester (57) was converted to target inhibitor (59) by reaction with BOC anhydride (53%) and to target inhibitor (58) by reaction with carbonate reagent (47) (62%).

Figure 9:
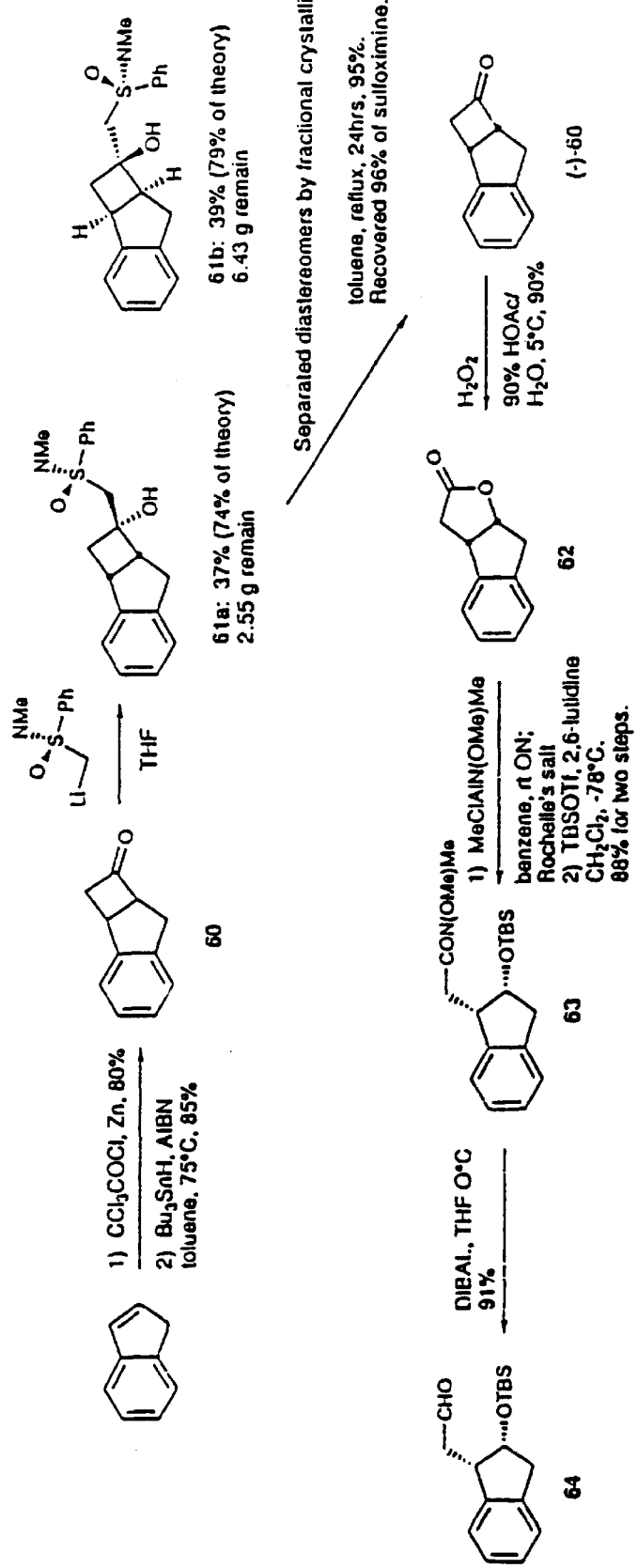
FIG. 9 shows a representative synthesis of chemical intermediate (64).

Cycloaddition of dichloroketene (generated in situ from trichloroacetyl chloride and zinc) with indene (80%), followed by tributyltin hydride reduction (85%) resulted in cyclobutanone (60) (FIG. 9). Coupling of ketone (60) with the lithium anion of the Johnson sulfoximine gave a mixture of diastereomeric alcohols (61a) (37%) and (61b) (39%). These diastereomers were separated by fractional crystallization. Compound (61a) was heated in toluene for 24 hours to afford optically pure cyclobutanone (—)—(60) (95%). Oxidation ($H_2O_2$, acetic acid/water, 9:1) then provided lactone (62) (90%). Conversion to the Weinreb amide was followed by protection of the newly generated hydroxyl group as its TBS ether to give compound (63) (88% for two steps). Reduction with diisobutylaluminum hydride (DIBAL) (DIBAL, THF, 0° C., 91%) resulted in aldehyde (64).

Figure 10:
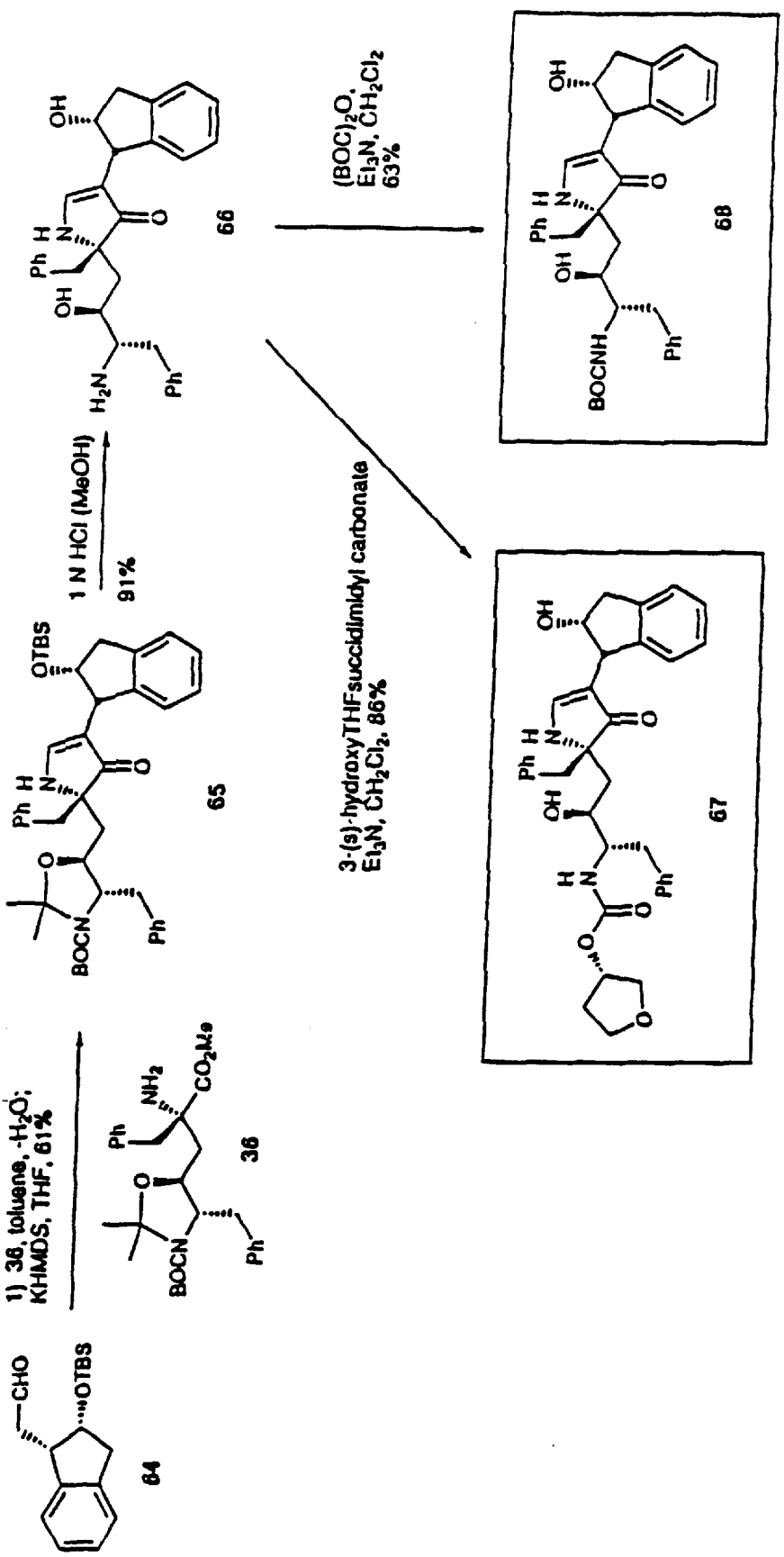
FIG. 10 shows a representative synthesis of compounds (67) and (68).

Pyrrolinone cyclization of aldehyde (64) with aminoester (36), as shown in FIG. 10, was accomplished by condensation followed by treatment with KHMDS (61%). The resulting pyrrolinone (65) was subjected to treatment with 1 N HCl in methanol to give amine (66) (91%). Target HIV-1 protease inhibitors (67) and (68) were then obtained by treatment with carbonate (47) (86%) and BOC anhydride (63%), respectively.

Alternatively, amino ester (21) can be prepared from L-prenylglycine. The present inventors have discovered that the stereoselective alkylation, with suitably protected electrophiles, of novel oxazolidinones derived from L-prenylglycine leads to an effective synthesis of amino ester building blocks incorporating functionalized amino acid side chain precursors. This method provides improved access to pyrrolinones with DNA-encoded and non-DNA-coded side chains and, thus, affords important flexibility in peptidomimetic design. In accordance with this methodology (which is exemplified in FIGS. 11–14), an amino acid of formula (I):

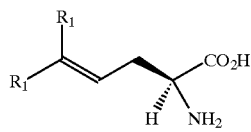

(I)

wherein each $R_1$ is, independently, an alkyl group having from 1 to about 10 carbon atoms; is reacted with base, a compound of the formula $R_2-C(=O)H$, wherein $R_2$ is an alkyl group having from 1 to about 10 carbon atoms or an aryl group having from about 3 to about 10 carbon atoms, and a compound of the formula $R_3-X$, wherein $R_3$ is an amine protecting group and X is a halogen atom or a suitable leaving group to produce novel oxazolidinone compounds of formula (II):

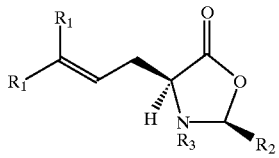

(II)

Bases which can be used in such procedures include, for example, sodium hydroxide, potassium hydroxide and lithium hydroxide, with sodium hydroxide being preferred. Useful amine protecting groups, represented by $R_3$, include, for example, allyloxycarbonyl (Alloc), benzyloxycarbonyl (CBz), and chlorobenzyloxycarbonyl groups, with the allyloxycarbonyl group being preferred. X may be a suitable leaving group including, for example, a mixed anhydride group (e.g., CBz-O-CBz), a succinimide group (e.g., AllocOSu) or a halogen atom, with a chlorine atom being preferred. $R_2$ is preferably a t-butyl group or a benzyl group, with a t-butyl group being more preferred. Each $R_1$ is preferably a methyl group.

Thereafter, oxazolidinone compounds of formula (II) are reacted in the presence of base and a compound of the formula R6—Z, wherein Z is a halogen atom, an epoxide electrophile or a suitable leaving group and $R_6$ is a side chain of a natural or unnatural amino acid, to produce a compound of formula (III):

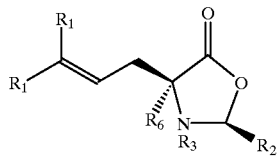

(III)

wherein $R_1$, $R_2$, $R_3$ and $R_6$ are as defined above. Representative examples of this reaction sequence are presented in FIGS. 13 and 14. Bases which can be used in such procedures include, for example, sodium bis(trimethylsilyl)amide (NaHMDS), potassium bis(trimethylsilyl)amide (KHMDS), lithium bis(trimethylsilyl)amide (LiHMDS) and lithium diisopropyl amine (LDA), with KHMDS being preferred. Representative natural and unnatural amino acids, represented by R6, include, for example, alanine, histidine, serine, tryptophan, tyrosine, arginine, cysteine, glutamic acid, alkylalanine, cyclohexylalanine, 1-naphthylalanine, 2-naphthylalanine, 9-anthrylalanine, fluorophenylalanine, pyridylalanine and dopa. Z may a halogen atom, an epoxide electrophile or a suitable leaving group including, for example, a tosyl group, a mesyl group or a triflyl group; with a bromine atom or an iodine atom being more preferred.

In another embodiment of the present invention, oxazolidinone compounds of formula (II) can be reacted in the presence of base and a compound of formula $N\equiv CCH_2Br$ or $N\equiv CCH=CH_2$ to produce a compound of the formula (IV)

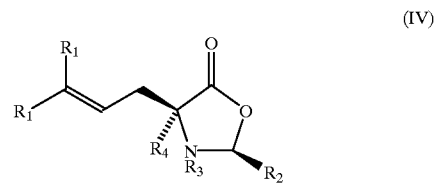

(IV)

wherein $R_1$, $R_2$, $R_3$ and R4 are as defined above. Compounds of formula (IV) can be hydrolyzed with aqueous acid to produce a further compound of formula (IV) wherein $R_4$ is the side chain of a natural or unnatural amino acid, preferably selected from the group consisting of asparagine and glutamine. Representative examples of this reaction sequence are presented in FIG. 13. Bases which can be used in such procedures include, for example, sodium bis(trimethylsilyl)amide (NaHMDS), potassium bis(trimethylsilyl)amide (KHMDS), lithium bis(trimethylsilyl)amide (LiHMDS) and lithium diisopropyl amine (LDA), with potassium bis(trimethylsilyl)amide (KHMDS) being preferred. Any strong aqueous acid may be used in such procedures including, for example, sulfuric acid, hydrochloric acid, nitric acid and phosphoric acid, with sulfuric acid being preferred.

In another embodiment of the present invention, compounds of formula (V):

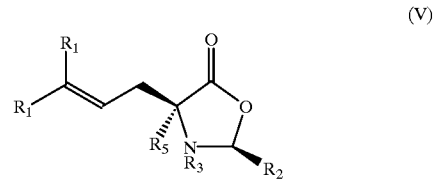

(V)

wherein each $R_1$ is, independently, an alkyl group having from 1 to about 10 carbon atoms;

$R_2$ is an alkyl group having from 1 to about 10 carbon atoms or an aryl group having from about 3 to about 10 carbon atoms;

$R_3$ is an amine protecting group; and $R_5$ is a side chain of a natural or unnatural amino acid, are reacted with base to produce compounds of formula (VI):

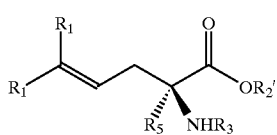

(VI)

wherein $R_1$, $R_3$ and $R_5$ are as defined above, and $R_2$ is an alkyl group having from 1 to about 10 carbon atoms or an aryl group having from about 3 to about 10 carbon atoms.

Bases which can be used in such procedures include, for example, lithium hydroxide and potassium hydroxide, with 3N potassium hydroxide being most preferred. Useful amine protecting groups, representing $R_3$ include, for example, allyloxycarbonyl (Alloc), benzyloxycarbonyl (Cbz), and chlorobenzyloxycarbonyl groups, with the allyloxycarbonyl group being preferred. Side chains of natural or unnatural amino acids may be used including, for example, alanine, histidine, serine, tryptophan, tyrosine, asparagine, glutamine, lysine, arginine, cysteine, glutamic acid, aspartic acid, methionine, alkylalanine, cyclohexylalanine, 1-naphthylalanine, 2-naphthylalanine, 9-anthrylalanine, fluorophenylalanine, pyridylalanine, dopa, norlysine, homolysine and homoserine. $R_2$ is preferably a benzyl group or a t-butyl group, with a t-butyl group being more preferred. $R_2$, is preferably a methyl group. Each $R_1$ is preferably a methyl group.

Subsequently, compounds of formula (VI) can be reacted in the presence of catalyst to produce a compound of formula (VII):

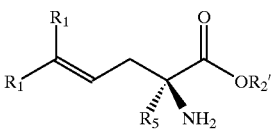

(VII)

wherein $R_1$, $R_2$, and $R_5$ are as defined above. Representative examples of this reaction are presented in FIGS. 12–14. Catalysts which can be used in such procedures include, for example, $Pd(Ph_3P)_4$, $Pd_2(dba)_3$, $(Ph_3P)_2PdCl_2$, $(C_6H_5CN)_2PdCl_2$, $(CH_3CN)_2PdCl_2$, $(CH_3CO_2)_2Pd(Ph_3P)_2$, with $Pd(Ph_3P)_4$ being preferred. When $R_3$ is Alloc, the catalyst may preferably be $Pd_2(dba)_3$ or $Pd(Ph_3P)_4$ in the presence of dimedone, or the catalyst may be $(Ph_3P)_2PdCl_2$, $(C_6H_5CN)_2PdCl_2$, $(CH_3CN)_2PdCl_2$, or $(CH_3CO_2)_2Pd(Ph_3P)_2$ in the presence of $Bu_3SnH$. Alternatively, when $R_3$ is CBz, the catalyst may be any hydrogenation catalyst, that will not react with the prenyl group, in the presence of hydrogen.

In accordance with the present invention, natural or unnatural amino acid side chains may be bound to a suitable protecting group at any or all points in the reaction sequence. Suitable protecting groups for any particular natural or unnatural amino acid are well known to those skilled in the art. Moreover, a protecting group can be removed from a natural or unnatural amino acid side chain at any point in the reaction sequence, as desired, by methods well known by those skilled in the art. Examples of suitable protecting groups for the natural or unnatural amino acid side chains and methods for protecting and deprotecting the natural or unnatural amino acid side chains are included, for example, in FIGS. 13 and 14.

The present invention is also directed to novel oxazolidinone compounds of the formula:

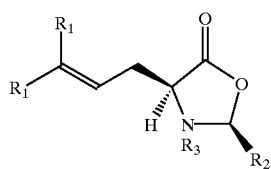

wherein
each $R_1$ is, independently, an alkyl group having from 1 to about 10 carbon atoms;
$R_2$ is an alkyl group having from 1 to about 10 carbon atoms or an aryl group having from about 3 to about 10 carbon atoms, and
$R_3$ is an amine protecting group.

Preferably, each $R_1$ is a methyl group. A preferred $R_2$ group is a t-butyl group or a benzyl group, with a t-butyl group being more preferred. Useful amine protecting groups, represented by $R_3$, include, for example, allyloxycarbonyl (Alloc), benzyloxycarbonyl (CBz), and chlorobenzyloxycarbonyl groups, with the allyloxycarbonyl group being preferred.

The pyrrolinone-based compounds of the invention contain amino groups and, therefore, are capable of forming salts with various inorganic and organic acids. Such salts are also within the scope of this invention. Representative salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, propionate, succinate, sulfate, tartrate, tosylate, and undecanoate. The salts can be formed by conventional means, such as by reacting the free base form of the product with one or more equivalents of the appropriate acid in a solvent or medium in which the salt is insoluble, or in a solvent such as water which is later removed in vacuo or by freeze drying. The salts also can be formed by exchanging the anions of an existing salt for another anion on a suitable ion exchange resin.

The present invention also provides prophylactic, diagnostic, and therapeutic compositions comprising one or more pyrrolinone-based compounds. By administering an effective amount of such compositions, for example, prophylactic or therapeutic responses can be produced in a human or some other type mammal. It will be appreciated that the production of prophylactic or therapeutic responses includes the initiation or enhancement of desirable responses, as well as the cessation or suppression of undesirable responses.

Compositions for use in the methods of this invention can be in the form of a solid, semisolid or liquid form and can include one or more of pyrrolinone-based compounds as an active ingredient in admixture with an organic or inorganic carrier or excipient suitable for external, enteral or parenteral applications. The active ingredient can be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes maybe used. The active ingredient is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine can be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type can also be employed as fillers in gelatin capsules; preferred materials in this connection also include lactose or milk sugar as well as high molecular weight polyethylene glycols. When aqueous suspensions and/or elixirs are desired for oral administration, the active ingredient can be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of pyrrolinone-based compounds in either sesame or peanut oil or in aqueous propylene glycol can be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is possible to administer the compounds of the present invention topically when treating inflammatory conditions of the skin and this can preferably be done by way of creams, jellies, gels, pastes, ointments and the like, in accordance with standard pharmaceutical practice.

The amount of active ingredient that can be combined with the carrier materials to produce a single dosage form will vary depending upon the host treated and the particular mode of administration. The specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range can be more than adequate, while in other cases still larger doses can be employed without causing any harmful side effects provided that such higher dose levels are first divided into several small doses for administration throughout the day.

Additional objects, advantages and novel features of this invention will become apparent to those skilled in the art upon examination of the following examples, which are not intended to limit the scope of the present invention.

EXAMPLE 1

Synthesis of Oxazolidinones

Initially, L-prenylglycine was prepared by alkylating (R,R)-(−)-pseudoephedrine glycinamide (II(−)-6 in FIG. 11) with prenyl bromide, LDA, LiCl and THF, and subsequently hydrolyzing the pseudoephedrine auxiliary. L-prenylglycine was produced as a white solid at a yield of 63% and 94% ee by HPLC: $[\alpha]_D^{23}$ −4.0° (c 1.03, 1 N aq HCl); IR (KBr) 3420 (w), 3300–2400 (s), 2110 (w), 1590 (s), 1520 (s), 1430 (s), 1400 (s), 1360 (m), 1320 (m), 1300 (m), 1150 (m) cm-1; $^1$H NMR (500 MHZ, $D_2O$) δ 5.04 (apparent t, J=7.5 HZ, 1H), 3.63 (m, 1 H), 2.50 (m, 2 H), 1.67 (s, 3 H), 1.58 (s, 3 H); $^{13}$C NMR (125 MHZ, $D_2O$; DSS) δ 177.2, 141.6, 118.8, 57.4, 31.8, 27.7, 19.8; high resolution mass spectrum (Cl, $NH_3$) m/z 144.1026 [(M+H)$^+$; calcd for $C_7H_{14}NO_2$: 144.1024].

Subsequently, the sodium salt of L-prenylglycine was condensated with pivaldehyde via the protocol described in Seebach et al, Helv. Chim. Acta, 1985 68, 1243. Thereafter, the resultant imine was treated with allyl chloroformate to induce cyclization to produce the novel oxazolidinone compounds (II(+)-2a and II(+)-2b in FIG. 11) as a 2:1 mixture of cis and trans diastereomers in a yield of 64%. The pure cis isomer was obtained in 43% yield after silica gel flash chromatography: colorless oil; $[\alpha]_D^{23}$ +46.8° (c 1.03, $CHCl_3$); IR ($CHCl_3$) 2980 (m), 2910 (m), 1795 (s), 1720 (s), 1390 (m), 1335 (m), 1045 (m), 980 (m) cm$^{-1}$; $^1$H NMR (500 MHZ, $CDCl_3$) δ 5.90 (m, 1 H), 5.51 (s, 1 H), 5.30 (m, 3 H), 4.62 (m, 2 H), 4.24 (dd, J=8.0, 6.7 Hz, 1 H), 2.58 (m, 2 H), 1.72 (s, 3 H), 1.63 (s, 3 H), 0.97 (s, 9 H); $^{13}$C NMR (125 MHZ, $CDCl_3$) δ 172.3, 155.8, 135.0, 131.8, 118.9, 118.5, 96.2, 67.0, 57.5, 37.0, 31.8, 29.7, 25.8, 25.0, 17.9; high resolution mass spectrum (Cl, $NH_3$) m/z 296.1858 [(M+H)$^+$; calcd for $C_{16}H_{26}NO_4$: 296.1861]. Anal. Calcd for $C_{16}H_{25}$, $NO_4$: C, 65.06; H, 8.53; N, 4.74. Found: C, 64.96; H, 8.38; N, 4.74.

EXAMPLE 2

Synthesis of a Functionalized Oxazolidinone Compound

Figure 11:
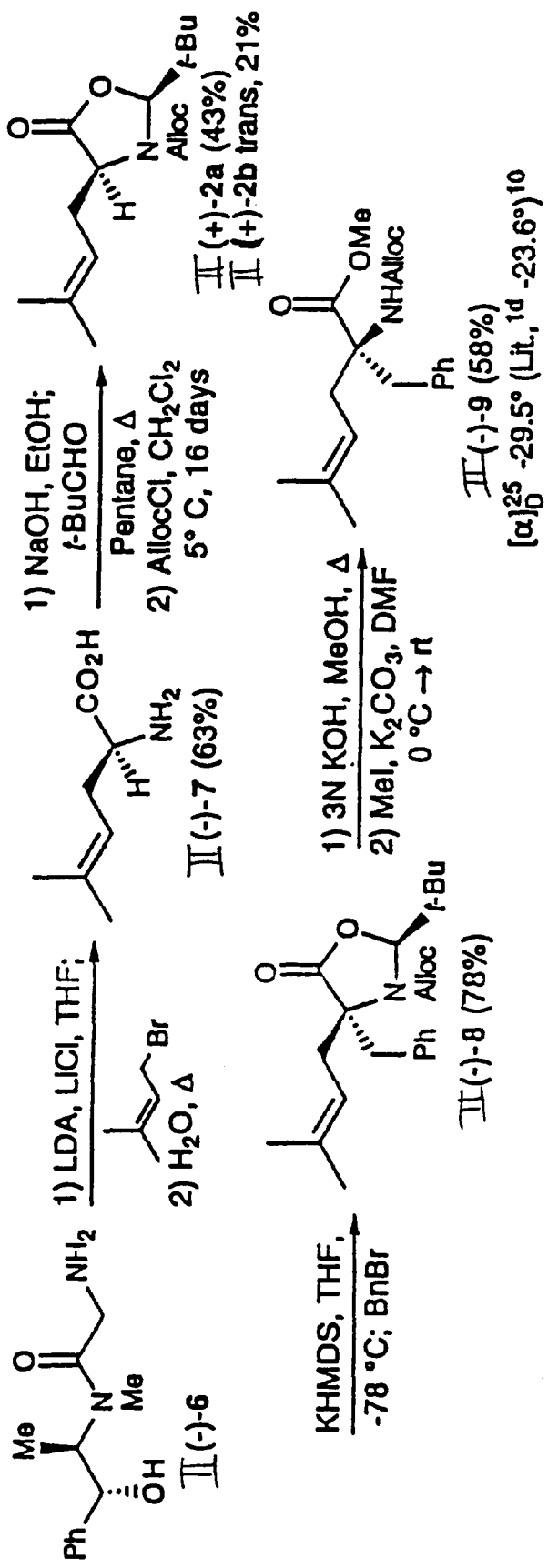
FIG. 11 shows a representative synthesis of acyclic olefinic synthons from oxazolidinone compounds derived from L-prenylglycine.

To test the utility of the novel oxazolidinone compound in Example 2, the amino ester building block for pyrrolinones bearing the phenylalanine side chain was prepared, as in FIG. 11. Stereoselective alkylation of the novel oxazolidinone compounds with benzyl bromide, basic hydrolysis of the alkylated oxazolidinone, and O-methylation of the resultant acid yielded the protected amino ester. This protected amino ester was identical with material derived from D-phenylalanine.

EXAMPLE 3

Synthesis of Functionalized Oxazolidinone Compounds

The novel oxazolidinone compound was alkylated with either p-benzyloxybenzyl bromide, benzyloxymethyl chloride or 1,4-diiodobutane. In each case, alkylation proceeded with high diastereoselectivity (greater than 95%). The unwanted diastereomers could not be detected by $^1$H NMR.

Figure 12:
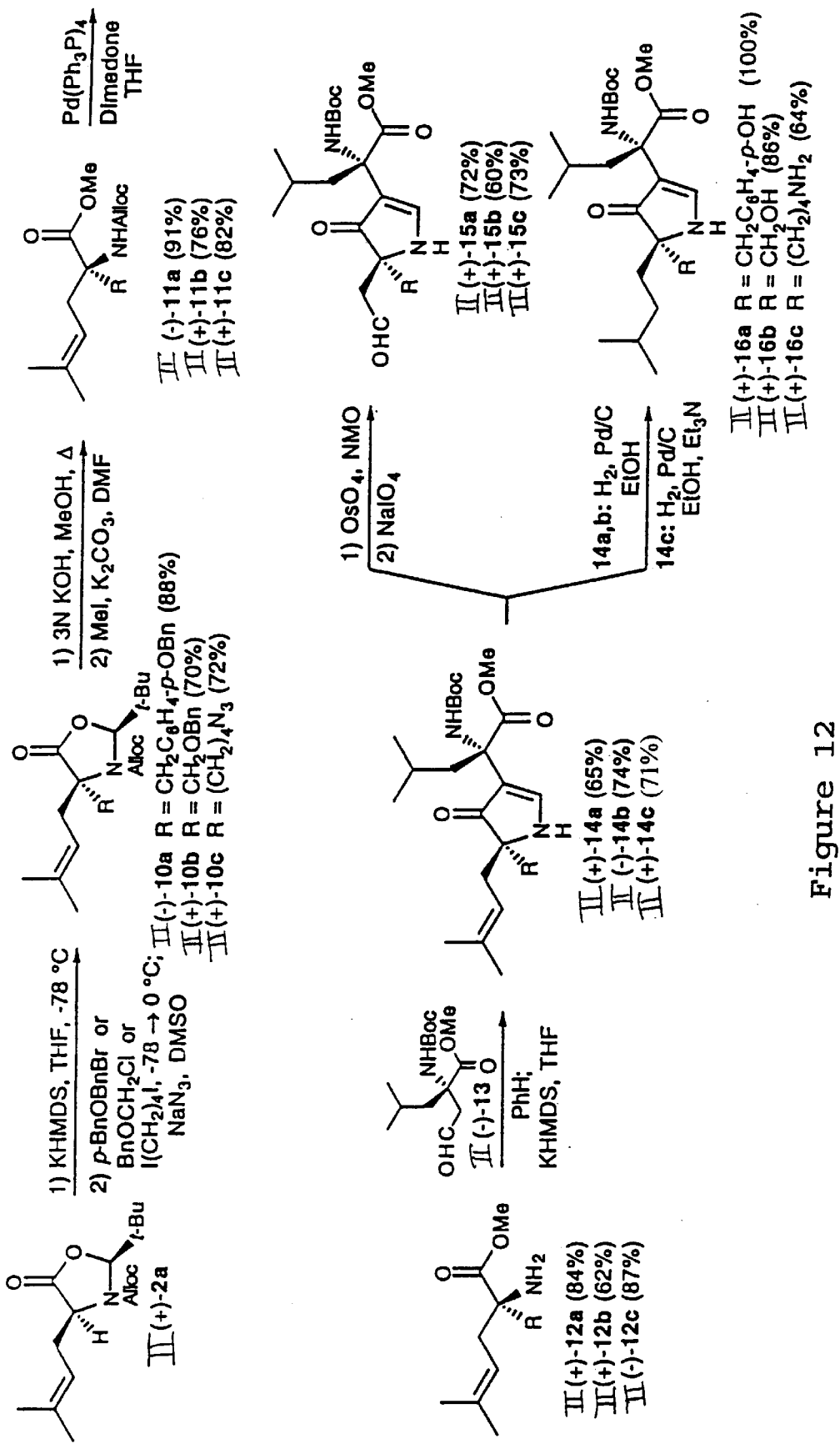
FIG. 12 shows syntheses of compounds comprising a tyrosine side chain, a serine side chain or a lysine side chain via N-terminal and C-terminal cyclizations.

For the lysine mimetic, the intermediate primary iodide was treated with $NaN_3$ in DMSO to generate the primary azide in a high yield (II(+)-10c in FIG. 12). Basic hydrolysis of the alkylated oxazolidinones, identified as compounds II(−)-10a, II(+)-10b and II(+)-10c in FIG. 12, followed by O-methylation of the resultant acids then provided the protected amino esters, identified as compounds II(−)-11a, II(+)-11b and II(+)-11c in FIG. 12. Palladium-catalyzed removal of the allyloxycarbonyl (Alloc) protecting groups provided the amino esters, identified as compounds II(+)-12a, II(+)-12b and II(−)-12c in FIG. 12. Properties of compound II(+)-12a: light yellow wax; $[\alpha]_D^{23}$ +4.0° (c 1.13, $CHCl_3$); IR ($CHCl_3$) 3010 (m), 2960 (m), 2940 (m), 1735

(s), 1615 (m), 1510 (s), 1455 (m), 1230 (s), 1180 (s) cm$^{-1}$; $^1$H NMR (500 MHZ, CDCl$_3$) δ 7.33 (m, 5 H), 7.05 (d, J=8.6 Hz, 2 H), 6.87 (d, J=8.6 Hz, 2 H), 5.04 (apparent t, J=7.6 Hz, 1 H), 5.01 (s, 2 H), 3.67 (s, 3 H), 3.11 (d, J=13.4 Hz, 1 H), 2.72 (d, J=13.4 Hz, 1 H), 2.56 (dd, J=14.0, 6.7 Hz, 1 H), 2.33 (dd, J=14.1, 8.5 Hz, 1 H), 1.70 (s, 3 H), 1.64 (s, 3 H), 1.61 (s, 2 H); $^{13}$C NMR (125 MHZ, CDCl$_3$) δ 177.0, 157.9, 137.1, 136.3, 130.8, 128.8, 128.5, 127.9, 127.4, 118.0, 114.8, 70.0, 62.7, 51.8, 45.0, 38.6, 26.0, 18.1; high resolution mass spectrum (CI, NH$_3$) m/z 354.2076 [(M+H)$^+$; calcd for C$_{22}$H$_{28}$NO$_3$: 354.2069]. Anal. Calcd for C$_{22}$H$_{27}$NO$_3$: C, 74.76; H, 7.70; N, 3.97. Found: C, 74.52; H, 7.72; N, 3.79.

Compounds II(+)-12a, II(+)-12b and II(−)-12c were condensed with an aldehyde building block derived from D-leucine, identified as compound II(−)-13 in FIG. 12. Cyclization of the corresponding imines with KHMDS (4 equiv) in THF afforded the protected pyrrolinones, identified as compounds II(+)-14a, II(−)-14b and II(+)-14c in FIG. 12. The protected pyrrolinones were produced in yields of 65–74%, which is comparable to those obtained with chemically inert side chains. Properties of compound II(+)-14a: white foam; $[\alpha]_D^{23}$ +50.9° (c 1.03, CHCl$_3$); IR (CHCl$_3$) 3450 (w), 3320 (w), 3010 (m), 2980 (m), 1705 (s), 1510 (s), 1235 (s), 1170 (s) cm$^{-1}$; $^1$H NMR (500 MHZ, CDCl$_3$) δ 7.87 (s, 1 H), 7.32 (m, 5 H), 6.99 (d, J=8.5 Hz, 2 H), 6.94 (s, 1 H), 6.81 (d, J=8.6 Hz, 2 H), 5.31 (s, 1 H), 5.00 (s, 2 H), 4.97 (apparent t, J=7.3 Hz, 1 H), 3.59 (s, 3 H), 2.87 (d, J=13.8 Hz, 1 H), 2.75 (d, J=13.8 Hz, 1 H), 2.34 (dd, J=14.4, 7.4 Hz, 1 H), 2.26 (dd, J=14.4, 7.3 Hz, 1 H), 2.17 (m, 1 H), 2.00 (m, 1 H), 1.64 (s, 3 H), 1.55 (m, 1 H), 1.54 (s, 3 H), 1.38 (s, 9 H), 0.85 (d, J=6.7 Hz, 3 H), 0.82 (d, J=6.6 Hz, 3 H); $^{13}$C NMR (125 MHZ, CDCl$_3$) δ 201.2, 173.6, 161.8, 157.7, 154.4, 137.0, 136.1, 131.0, 128.6, 128.0, 127.4, 117.0, 114.4, 78.8, 71.1, 70.0, 59.8, 52.4, 42.4, 40.9, 34.6, 28.4, 25.8, 24.3, 24.2, 23.5, 18.0; high resolution mass spectrum (CI, NH$_3$) m/z 591.3451 [(M+H)$^+$; calcd for C$_{35}$H$_{47}$N$_2$O$_6$: 591.3434].

A two-step oxidation process, using OsO$_4$ and NMO followed by NaIO$_4$, produced aldehydes, identified as compounds II(+)-15a, II(+)-15b and II(+)-15c in FIG. 12, which were suitable for chain extension to polypyrrolinones. Properties of compound II(+)-15a: colorless oil; $[\alpha]_D^{23}$ +115.4° (c 0.68, CHCl$_3$); IR (CHCl$_3$) 3450 (m), 3010 (m), 2960 (m), 1710 (s), 1510 (s), 1490 (s), 1240 (s), 1175 (s) cm$^{-1}$; $^1$H NMR (500 MHZ, CDCl$_3$) δ 9.50 (s, 1 H), 7.93 (s, 1 H), 7.34 (m, 5 H), 6.99 (d, J=8.6 Hz, 2 H), 6.82 (d, J=8.6 Hz, 2 H), 6.44 (s, 1 H), 6.03 (s, 1 H), 5.00 (s, 2 H), 3.62 (s, 3 H), 2.89 (s, 2 H), 2.75 (d, J=16.9 Hz, 1 H), 2.61 (d, J=17.0 Hz, 1 H), 2.31 (m, 1 H), 1.83 (m, 1 H), 1.53 (sept, J=6.5 Hz, 1 H), 1.36 (s, 9 H), 0.86 (d, J=6.7 Hz, 3 H), 0.79 (d, J=6.7 Hz, 3 H); $^{13}$C NMR (125 MHZ, CDCl$_3$) δ 199.6, 199.2, 173.1, 162.3, 157.9, 154.0, 136.9, 131.0, 128.6, 128.0, 127.4, 126.9, 114.5, 112.3, 79.0, 70.0, 68.0, 58.9, 52.6, 48.7, 42.0, 40.6, 29.7, 28.3, 24.2, 24.0, 23.4; high resolution mass spectrum (Cl, NH3) m/z 565.2905 [(M+H)$^+$; calcd for C$_{32}$H$_{41}$,N$_2$O$_7$: 565.2913].

Alternatively, the side chains in compounds II(+)-14a, II(−)-14b and II(+)-14c in FIG. 12 were unmasked via catalytic hydrogenolysis, which reduced the terminal prenyl group to produce compounds II(+)-16a, II(+)-16b and II(+)-16c in FIG. 12. The successful generation of the lysine aminobutyl moiety required the inclusion of triethylamine, whereas the deprotection of the tyrosine and serine side chains proceeded cleanly and rapidly. Properties of II(+)-16a: white glass; $[\alpha]_D^{23}$ +77.5° (c 1.27, CHCl$_3$); IR (CHCl$_3$) 3450 (m), 3330 (m), 3010 (m), 2960 (s), 1705 (s), 1520 (s), 1495 (s), 1370 (m), 1240 (s), 1215 (s), 1175 (s) cm$^{-1}$; $^1$H NMR (500 MHZ, CDCl$_3$) δ 7.92 (s, 1 H), 6.92 (d, J=8.1 Hz, 2 H), 6.71 (d, J=8.2 Hz, 2 H), 6.41 (s, 1 H), 5.71 (s, 1 H), 3.63 (s, 3 H), 2.80 (d, J=13.7 Hz, 1 H), 2.69 (d, J=13.8 Hz, 1 H), 2.23 (m, 1 H), 1.95 (m, 1 H), 1.75 (m, 2 H), 1.51 (m, 3 H), 1.37 (s, 9 H), 0.96 (m, 2 H), 0.85 (d, J=6.7 Hz, 3 H), 0.81 (d, J=6.6 Hz, 3 H), 0.78 (d, J=6.6 Hz, 3 H), 0.76 (d, J=6.6 Hz, 3 H); $^{13}$C NMR (125 MHZ, CDCl$_3$) δ 201.3, 173.7, 162.3, 155.1, 154.4, 131.1, 127.0, 115.1, 111.6, 79.0, 71.5, 59.6, 52.6, 42.3, 34.0, 31.5, 28.4, 28.2, 24.2, 23.5, 22.4; high resolution mass spectrum (Cl, NH$_3$) m/z 503.3124 [(M+H)$^+$; calcd for C$_{28}$H$_{43}$N$_2$O$_6$: 503.3121].

Various modifications of the invention, in addition to those described herein, will be apparent to those skilled in the art from the foregoing description. Such modifications are intended to fall within the scope of the appended claims.

What is claimed is:

1. A synthetic method comprising the steps of:

reacting a compound of formula (I):

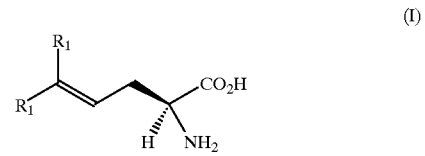

(I)

wherein each R$_1$ is methyl; in the presence of a first base selected from the group consisting of sodium hydroxide, potassium hydroxide, and lithium hydroxide; with:

a compound of the formula R$_2$—C(=O)H wherein R$_2$ is t-butyl or benzyl; and a compound of the formula R$_3$—X, wherein R$_3$ is an allyloxycarbonyl group, and X is a halogen atom or a leaving group;

thereby producing a compound of formula (II):

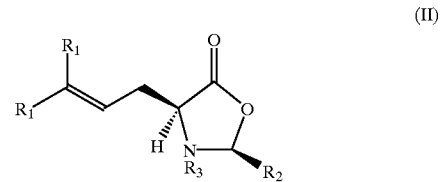

(II)

wherein R$_1$, R$_2$ and R$_3$ are as defined above; and reacting the compound of formula (II) in the presence of a second base selected from the group consisting of sodium bis(trimethylsilylamide), potassium bis(trimethylsilylamide), lithium bis(trimethylsilylamide) and lithium diisopropylamine; with a compound of the formula R$_6$—Z wherein Z is a halogen atom or a leaving group and R$_6$ is a side chain of a natural or unnatural amino acid, thereby producing a compound of formula (III):

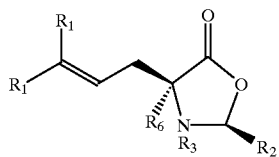

(III)

wherein $R_1$, $R_2$, $R_3$ and $R_6$ are as defined above.

2. The method of claim 1, wherein said natural or unnatural amino acid is selected from the group consisting of alanine, histidine, serine, tryptophan, tyrosine, arginine, cysteine, glutamic acid, alkylalanine, lysine, aspartic acid, methionine, cyclohexylalanine, 1-naphthylalanine, 2-naphthylalanine, 9-anthrylalanine, fluorophenylalanine, pyridylalanine and dopa.

3. The method of claim 1 wherein $R_2$ is benzyl.

4. The method of claim 1 wherein $R_2$ is t-butyl.

5. The method of claim 1 wherein said first base is sodium hydroxide and said second base is potassium bis(trimethylsilyl)amide.

* * * * *